US006576741B1

(12) United States Patent
Åkesson et al.

(10) Patent No.: US 6,576,741 B1
(45) Date of Patent: Jun. 10, 2003

(54) STREPTOCCAL INHIBITOR OF COMPLEMENT-MEDIATED LYSIS, PROTEIN SIC

(75) Inventors: Per Åkesson, Lund (SE); Lars Björck, Lund (SE); Anders Sjoholm, Lund (SE)

(73) Assignee: Hansa Medical AB, Lund (SE)

( * ) Notice: Subject to any disclaimer, the term of this patent is extended or adjusted under 35 U.S.C. 154(b) by 0 days.

(21) Appl. No.: 09/051,380

(22) PCT Filed: Oct. 2, 1996

(86) PCT No.: PCT/SE96/01238

§ 371 (c)(1),
(2), (4) Date: Sep. 8, 1998

(87) PCT Pub. No.: WO97/13786

PCT Pub. Date: Apr. 17, 1997

(30) Foreign Application Priority Data

Oct. 9, 1995 (SE) ................................. 9503495

(51) Int. Cl.$^7$ ............................................ C07K 14/315

(52) U.S. Cl. ....................................................... 530/350

(58) Field of Search ........................ 530/350, 324–328, 530/820, 825

(56) References Cited

U.S. PATENT DOCUMENTS 5,180,810 A * 1/1993 Gomi et al.

FOREIGN PATENT DOCUMENTS

| EP | 367 890 A1 | 5/1990 |
| EP | 371 199 B1 | 10/1994 |
| WO | WO 91/19740 | 12/1991 |

OTHER PUBLICATIONS

Akesson et al., Journal of Biological Chemistry, 271 (2):1081–1088, Jan. 1996.*
Åkesson et al., "Protein H—A Novel IgG Binding Bacterial Protein," *Molecular Immunology* 26(6): 523–531, 1990.
Åkesson et al., "M1 protein and Protein H: IgGFc– and albumin–binding streptococcal surface proteins encoded by adjacent genes," *Biochem. Journal* 300: 877–886, 1994.
Ben Nasr et al., "Human kininogens interact with M protein, a bacterial surface protein and virulence determinant," *Biochem. Journal* 305: 173–180, 1995.
Berge and Björck, "Streptococcal Cysteine Proteinase Releases Biologically Active Fragments of Streptococcal Surface Proteins," *The Journal of Biological Chemistry* 270(17): 9862–9867, 1995.
Caparon and Scott, "Identification of a gene that regulates expression of M protein, the major virulence determinant of group A streptococci," *Proceedings of the National Academy of Science USA 84:* 8677–8681, 1987.
Chang et al., "Regulation of Complement Functional Efficiency by Histidine–Rich Glycoprotein," *Blood* 79(11): 2973–2980, 1992.
Chen and Cleary, "Complete Nucleotide Sequence of the Streptococcal C5a Peptidase Gene of *Streptococcus pyogenes*," *The Journal of Biological Chemistry* 265(6): 3161–3167, 1990.
Couser et al., "Complement and the direct mediation of immune glomerular injury: A new perspective," *Kidney International* 28: 879–890, 1985.
Dalbøge et al., "High–level expression of active human cystatin C in *Escherichia coli*," *Gene* 79: 325–332, 1989.
de Château and Björck, "Protein PAB, a Mosaic Albumin–binding Bacterial Protein Representing the First Contemporary Example of Module Shuffling," *The Journal of Biological Chemistry* 269(16): 12147–12151, 1994.
Fischetti, V., "Streptococcal M Protein: Molecular Design and Biological Behavior," *Clinical Microbiology Reviews* 2(3): 285–314, 1989.
Fischetti et al., "Conservation of a hexapeptide sequence in the anchor region of surface proteins from Gram–positive cocci," *Molecular Microbiology* 4(9): 1603–1605, 1990.
French et al., "Clusterin in renal tissue: preferential localization with the terminal complement complex and immunoglobulin deposits in glomeruli," *Clin. Exp. Immunol.* 88: 389–393, 1992.
Gomi et al., "The Gene Sequence and Some Properties of Protein H," *The Journal of Immunology* 144(10): 4046–4052, 1990.
Holm et al., "Aspects of Pathogenesis of Serious Group A Streptococcal Infections in Sweden, 1988–1989," *The Journal of Infectious Diseases* 166: 31–37, 1992.
Holm, S., "The pathogenesis of acute post–streptococcal glomerulonephritis in new lights," *Acta Pathol. Microbiol. Scand.* 96: 189–193, 1988.
Horstmann et al., "Antiphagocytic activity of streptococcal M protein: Selective binding of complement control protein factor H," *Proceedings of the National Academy of Science USA 85:* 1657–1661, 1988.

(List continued on next page.)

Primary Examiner—Marianne P. Allen
(74) Attorney, Agent, or Firm—Kalow & Springut LLP

(57) ABSTRACT

A protein from *Streptococcus pyogenes*, serotype M1 has been characterized. This protein, called protein SIC, plays a role in *S. pyogenes* pathogenicity and virulence. It inhibits hemolysis by interacting with the plasma proteins clusterin, and members of the cystatin protein super family such as hisitidine rich glycoprotein (HRG). The protein comprises at least one of the following partial amino acid sequences: (a) glu thr tyr thr ser arg asn phe; (b) asp trp ser gly asp asp trp pro glu asp asp trp; (c) arg ser gly val gly leu ser gln tyr gly trp ser; (d) trp ser ser asp lys lys asp glu thr glu asp lyr thr; (e) gly thr gly tyr glu lys arg asp asp trp gly gly pro gly; (f) lys arg asp asp trp arg gly pro gly his ile pro lys pro. The protein and antibodies specific for the protein can be used in analytical procedures for determining the present of virulent *Streptococcus pyrogens* in a sample. The protein can also be used in vaccine compositions.

1 Claim, 12 Drawing Sheets

OTHER PUBLICATIONS

Kehoe, M., *Bacterial Cell Wall,* J.–M Ghuysen and R. Hakenbeck (Eds.), Elsevier Science B.V., 1994, Chapter 11, "Cell–wall–associated proteins in Gram–positive bacteria," pp. 217–261.

Koide et al., "Amino Acid Sequence of Human Histidine–Rich Glycoprotein Derived from the Nucleotide Sequence of Its cDNA," *Biochemistry 25*(8): 2220–2225, 1986.

Mollnes et al., "Quantification of the Terminal Complement Complex in Human Plasma by an Enzyme–Linked Immunosorbent Assay Based on Monoclonal Antibodies against a Neoantigen of the Complex," *Scandinavian Journal of Immunology 22:* 197–202, 1985.

Morgan, P., "Complement membrane attack on nucleated cells: resistance, recovery and non–lethal effects," *Biochem. Journal 264:* 1–14, 1989.

Musser et al., "Geographic and Temporal Distribution and Molecular Characterization of Two Highly Pathogenic Glones of *Streptococcus pyogenes* Expressing Allelic Variants of Pyrogenic Exotoxin A (Scarlet Fever Toxin)," *The Journal of Infectious Diseases 167:* 337–346, 1993.

Nowak, R., "Flesh–Eating Bacteria: Not New, But Still Worrisome," *Science 264:* 1665, 1994.

Okada et al., "Membrane cofactor protein (CD46) is a keratinocyte receptor for the M protein of the group A streptococcus," *Proceedings of the National Academy of Science USA 92:* 2489–2493, 1995.

Pridmore et al., "New and versatile cloning vectors with kanamycin–resistance marker," *Gene 56:* 309–312, 1987.

Saigo et al., "Interaction of Histidine–rich Glycoprotein with Human T Lymphocytes," *The Journal of Biological Chemistry 264*(14): 8249–8253, 1989.

Saunders et al., "Clusterin depletion enhances immune glomerular injury in the isolated perfused kidney," *Kidney International 45:* 817–827, 1994.

Schneewind et al., "Sorting of Protein A to the Staphylococcal Cell Wall," *Cell 70:* 267–281, 1992.

Schneewind et al., "Structure of the Cell Wall Anchor of Surface Proteins in *Staphylococcus aureus,*" *Science 268:* 103–106, 1995.

Simpson et al., "Coregulation of Type 12 M Protein and Steptococcal C5a Peptidase Genes in Group A Streptococci: Evidence for a Virulence Regulation Controlled by the virR Locus," *Journal of Bacteriology 172*(2): 696–700, 1990.

Thern et al., "Ig–Binding Surface Proteins of *Streptococcus pyogenes* also Bind Human C4b–Binding Protein (C4BP), a Regulatory Component of the Complement System," *The Journal of Immunology 154:* 375–386, 1995.

Tschopp and French, "Clusterin: modulation of complement function," *Clin. Exp. Immunol. 97*(suppl. 2): 11–14, 1994.

Tschopp et al., "Clusterin, the Human Apolipoprotein and Complement Inhibitor, Binds to Complement C7, C8β, and the b Domain of C9," *Journal of Immunology 151:* 2159–2165, 1993.

Wexler et al., "Human Neutrophil Chemotactic Response to Group A Streptococci: Bacteria–Mediated Interference with Complement–Derived Chemotactic Factors," *Infection and Immunity 39*(1): 239–246, 1983.

Wexler et al., "Mechanism of action of the group A streptococcal C5a inactivator," *Proceedings of the National Academy of Science USA 82:* 8144–8148, 1985.

Wilson and Easterbrook–Smith, "Clusterin binds by a multivalent mechanism to the Fc and Fab regions of IgG," *Biochimica et Biophysica Acta 1159:* 319–326, 1992.

Yanisch–Perron et al., "Improved M13 phage cloning vectors and host strains: nucleotide sequences of the M13mp18 and pUC19 vectors," *Gene 33:* 103–119, 1985.

\* cited by examiner

```
protein SIC (strain AP1)      ETYTSRNF-- ---DWSGDDW PEDDWSGDGL SKYDRSGVGL SQYGWSQYGW
protein SIC (strain 1034)     ETYTSRNFDW SGDDWSGDDW PEDDWSGDGL SKYDRSGVGL SQYGWSHYGW protein SIC (strain AP1)      SSDKEEWPED WPEDDWSSDK KDETEDKTRP PYGEALGTGY EKRDDWGGPG
protein SIC (strain 1034)     SSDKEEWPED WPEDDWSSDK KDETEDKTRP PYGEALGTGY EKRDDWGGPG protein SIC (strain AP1)      TVATDPYTPP YGGALGTGYE KRDDWGGPGT VATDPYTPPY GEALGTGYEK
protein SIC (strain 1034)     TVATDPYTPP YGGALGTGYE KRDDWGGPGT VATDPYTPPY GGALGTGYEK protein SIC (strain AP1)      RDDWRGPGHI PKPENEDSPN PSHIPEPRQI EWPQWN---- GFDELSFGPS
protein SIC (strain 1034)     RDDWRGPGHI PKPENDDSPN PSHIPEPRHI EWPQWELAFD GFDELSFGPS protein SIC (strain AP1)      DWGQSEDAPR FPSEPRVPEK PQHTPQKNPQ ESDFDRGFSA GLKAKNSGRG
protein SIC (strain 1034)     DWGQSEDAPR FPSEPRVPEK PQHTPQKNPQ ESDFDRGFSA GLKAKNSGRG protein SIC (strain AP1)      IDFEGFQYGG WSDEYKKGYM QAFGTPYTPS AT
protein SIC (strain 1034)     IDFEGFQYGG WSDEYKKGYM QAFGTPYTPS AT
```

Fig. 11

```
protein SIC (strain 1004)   ETYTSRNFDW SGDDWSGDDW PEDDWSGDGL SKYDRSGVGL SQYGWSHYGW
protein SIC (strain AP1)    ETYTSRNF-- ---DWSGDDW PEDDWSGDGL SKYDRSGVGL SQYGWSQYGW protein SIC (strain 1004)   SSDK----EE WPEDDWSSDK KDETEDKTRP PYGEALGTGY EKRDDWGGPG
protein SIC (strain AP1)    SSDKEEWPED WPEDDWSSDK KDETEDKTRP PYGEALGTGY EKRDDWGGPG protein SIC (strain 1004)   TVATDPYTPP YGGALGTGYE KRDDWGGPG- ---------- ----------
protein SIC (strain AP1)    TVATDPYTPP YGGALGTGYE KRDDWGGPGT VAIDPYTPPY GEALGTGYEK protein SIC (strain 1004)   --------HI PKPENEQ--- ---------- ---------- ----------
protein SIC (strain AP1)    RDDWRGPGHI PKPENEQSPN PSHIPEPPQI EWPQWNGFDE LSFGPSDWGQ protein SIC (strain 1004)   ---------- ---------- ---------- ---------- ----------
protein SIC (strain AP1)    SEDAPRFPSE PRVPEKPQHT PQKNPQESDF DRGFSAGLKA KNSGRGIDFE protein SIC (strain 1004)   ---------- ---------- ---------
protein SIC (strain AP1)    GFQYGGWSDE YKKGYMQAFG TPYTPSAT
```

Fig. 12

STREPTOCCAL INHIBITOR OF COMPLEMENT-MEDIATED LYSIS, PROTEIN SIC

The present invention relates to a new protein, protein SIC, that can be derived from *Streptococcus pyogenes* strains of serotypes M1 and M57. Methods for analysis and purification and pharmaceutical preparations including vaccine compositions related to the protein as well as specific antibodies are also claimed.

*Streptococcus pyogenes* is an important human pathogen causing a number of acute suppurative infections such as erysipelas, necrotizing fasciitis, and pharyngitis. These Gram-positive bacteria also cause a serious toxic shock-like syndrome, whereas glomreulonephritis and rheumatic fever are serious poststreptococcal sequelae.

To elude the host defence and establish an infection, *S. pyogenes* has developed multiple molecular mechanisms. Some of these are dependent on genes located in a chromosomal region designated the mga locus according to a recent agreement, which is under the control of the positive regulator gene mga, previously called mry (Caparon and Scott, 1987: Proc. Natl. Acad. Sci. U. S. A. 84, 8677–8681) or virR (Simpson et al., 1990: J. Bacteriol. 172, 696–700).

Since the late 1980's unusually severe *S. pyogenes* infections have been reported world-wide. These hyperacute and often lethal infections have frequently been associated with the M1 serotype (Musser et al., 1993: J. Infect. Dis. 167, 337–346). This serotype is also connected with glomerulonephritis and rheumatic fever.

Based on structural variations in the antiphagocytic M protein (Fischetti, 1989: Clin. Microbiol. Rev. 2, 285–314; and Kehoe, 1994: New Compr. Biochem. 27, 217–261) *S. pyogenes* can be divided into more than 80 different serotypes. Most of these serotypes are rather harmless. However, during the last years, a lot of lethal streptococcal infections have been caused by strain belonging to the M1 serotype. Presently, because of the large amount of serotypes and the great similarity between these types, it is time-consuming and labourious to determine the serotype of a sample of *Streptococcus pyogenes*. Consequently, there is a need for simpler methods for determining whether a particular sample of *Streptococcus pyogenes* is virulent. There is also a need for better vaccines against virulent *Streptococcus pyogenes* strains.

SUMMARY OF THE INVENTION

A new protein from *Streptococcus pyogenes*, serotype M1, fulfilling the above mentioned needs has now been discovered and characterized. The protein and its corresponding gene has been obtained from strain AP1, which is of the M1 serotype.

In the mga locus of AP1, the regulatory gene mga is followed by emm1, the gene encoding the M1 protein. Immediately down-stream of emm1 is sph (Åkesson et al., 1994: Biochem. J. 300, 877–886), the gene encoding an IgGFc-binding M protein-related molecule called protein H (Åkesson et al., 1990: Mol. Immunol. 27, 523–531; Gomi et al., 1990: J. Immunol. 144, 4046–4052; WO 91/19740; EP 0 371 199). Located adjacent to sph is a previously uncharacterized gene. This gene constitutes one of the objects of the present invention.

The protein shows some variability and M1 serotype strains of *Streptococcus pyogenes* producing variants of protein SIC have also been isolated. When comparing the amino acid sequences of three different protein SIC variants, some conserved regions were found.

DETAILED DESCRIPTION OF THE INVENTION

The protein encoded by the uncharacterized gene as well as variants, subfragments and multiples of the protein having essentially the same antigenic and/or binding characteristics also constitutes an object of the present invention. The data obtained implicate that this extracellular protein plays a role in *S. pyogenes* pathogenicity and virulence through previously unknown molecular mechanisms. The new protein is referred to as protein SIC, Streptococcal Inhibitor of Complement-mediated lysis.

"SIC proteins" as utilized herein refers to streptococcal proteins which inhibit hemolysis by interacting with the plasma proteins clusterin and members of the cystatin protein superfamily, such as HRG, as demonstrated by affinity chromatography on a protein SIC Sepharose column or by indirect ELISA. SIC proteins may be distinguished from other proteins based upon criteria such as specific binding to the above mentioned plasma proteins and sequence homology. For example, SIC proteins of the present invention should comprise at least one of the following partial amino acid sequences:

a) glu thr tyr thr ser arg asn phe (SEQ ID NO:7);

b) asp trp ser gly asp asp trp pro glu asp asp trp (SEQ ID NO:8);

c) arg ser gly val gly leu ser gln tyr gly trp ser (SEQ ID NO:9);

d) trp ser ser asp lys lys asp glu thr glu asp lys thr (SEQ ID NO:10);

e) gly thr gly tyr glu lys arg asp asp trp gly gly pro gly (SEQ ID NO:11);

f) lys arg asp asp trp arg gly pro gly his ile pro lys pro (SEQ ID NO:12);

preferably the amino acid sequence of the SIC proteins should be at least 70% homologous, more preferably at least 85% homologous, still more preferably at least 90% homolgous and most preferably at least 95% homologous to anyone of the amino acid sequences disclosed in SEQ. ID. NOS 2, 3 and 4.

As already mentioned and suggested above, different variants of protein SIC have been isolated. Most isolates produced a variant showing close resemblance to protein SIC isolated from strain AP1, whose amino acid sequence is disclosed in SEQ. ID. NO. 2. However, two more variants having the amino acid sequences according to SEQ. ID. NO. 3 and SEQ. ID. NO. 4, respectively, have also been discovered. After aligning the sequences of the different variants the conserved partial sequences a)–f) above were found. Regions a)–e) are present in all known protein SIC variants. Protein SIC from one of the isolates only comprised a part of the f) region. Consequently the above regions are considered to have important functions in the protein.

By "subfragment" is meant a part-fragment of the given protein having essentially the same antigenic and/or binding characteristics. By "variants" is meant proteins or peptides in which the original amino acid sequence has been modified or changed by insertion, addition, substitution, inversion or exclusion of one or more amino acids. By "multiples" is meant those proteins containing multiples of the whole original protein or those protein containing multiples of subfragments and/or variants thereof.

The present invention also relates to nucleic acid sequences encoding protein SIC. As utilized within the context of the present invention, nucleic acid sequences which encode protein SIC are deemed to be substantially similar to those disclosed herein if: (a) the nucleic acid sequence is derived from the coding region of a native protein SIC gene (including, for example, variations of the sequences disclosed herein); (b) the nucleic acid sequence is capable of hybridization to nucleic acid sequences of the present invention under conditions of either moderate or high stringency (hybridization in 5×SSPE containing 0.1% SDS and 0.1 mg/ml ssDNA, at 50–65° C. dependent on the probe length, or 10–20° C. below the $T_m$ of the probe; washing in 1×SSPE, 0.1% SDS at 15–20° C. below the $T_m$ of the probe for moderate stringency, and in 0.1×SSPE, 0.1% at 10° C. below the $T_m$ of the probe for high stringency conditions) (see Sambrook et al., Molecular Cloning: A Laboratory Manual, 2nd Ed., Cold Spring Harbor Laboratory Press, NY, 1989); or (c) nucleic acid sequences are degenerate as a result of the genetic code to the nucleic acid sequences defined in (a) or (b). Furthermore, although nucleic acid molecules are primarily referred to herein, as should be evident to one of skill in the art given the disclosure provided herein, a wide variety of related nucleic acid molecules may also be utilized in various embodiments described herein, including for example, RNA, nucleic acid analogues, as well as chimeric nucleic acid molecules which may be composed of more than one type of nucleic acid.

Within another aspect of the present invention, probes and primers are provided for detecting nucleic acids sequences which encode protein SIC. Within one embodiment of the invention, probes are provided which are capable of hybridizing to protein SIC nucleic acids (DNA or RNA}. For purposes of the present invention, probes are "capable of hybridizing" to protein SIC nucleic acids if they hybridize to Sequence I.D. No 1, 5 or 6 under conditions of moderate or high stringency (see the section above concerning nucleic acid molecules, and Sambrook et al., supra); Preferably, the probe may be utilized to hybridize to suitable nucleotide sequences in the presence of 5×SSPE, 0.1% SDS, and 0.1 mg/ml ssDNA at 10–20° C. below the $T_m$ of the probe. Subsequent washes may be performed in 1×SSPE, 0.1% SDS at 15–20° C. for conditions of moderate stringency, and in 0.1×SSPE, 0.1% SDS at 10° C. below the $T_m$ of the probe for conditions of high stringency.

Probes of the present invention may be composed of either deoxyribonucleic acids (DNA) ribonucleic acids (RNA), nucleic acid analogues, or any combination of these, and may be as few as about 12 nucleotides in length, usually about 14 to 18 nucleotides in length, and possibly as large as the entire sequence which encodes protein SIC. Selection of probe size is somewhat dependent upon the use of the probe. For example, a long probe used under high stringency conditions is more specific, whereas a oligonucleotide carefully selected from the sequence can detect a structure of special interest.

Probes may be constructed and labeled using techniques which are well known in the art. Shorter probes of, for example, 12 or 14 bases may be generated synthetically. Longer probes of about 75 bases to less than 1,5 kb are preferably generated by, for example, PCR amplification in the presence of labeled precursors such as 32P-dCTP, digoxigenin-dUTP, or biotin-dATP. Probes of more than 1.5 kb are generally most easily amplified by transfecting a cell with a plasmid containing the relevant probe, growing the transfected cell into large quantities, and purifying the relevant sequence from the transfected cells (see Sambrook et al., supra).

Probes may be labeled by a variety of markers, including, for example, radioactive markers, fluorescent markers, enzymatic markers, and chromogenic markers. The use of 32P is particularly preferred for marking or labeling a particular probe.

As noted above, nucleic acid probes of the present invention may be utilized to detect the presence of protein SiC nucleic acid molecules within a sample. However, if such nucleic acids molecules are present in only a limited number, then it may be beneficial to amplify the relevant sequence such that it may be more readily detected or obtained.

A variety of methods may be utilized in order to amplify a selected sequence, including, for example, RNA amplification (see Lizardi et al., Bio/Technology 6:1197–1202, 1988; Kramer et al., Nature 339:401–402, 1989; Lomeli et al., Clinical Chem. 35(91) 1826–1831, 1989; U.S. Pat. No. 4,786,600), and nucleic acid amplification utilizing Polymerase Chain Reaction ("PCR") (see U.S. Pat. Nos. 4,683, 195, 4,683,202, and 4,800,159) (see also U.S. Pat. Nos. 4,876,187, and 5,011,769, which describe an alternative detection/amplification system comprising the use of scissile linkages). Within a particularly preferred embodiment, PCR amplilication is utilized to detect or obtain protein SIC nucleic acids. Briefly, as described in greater detail below, a nucleic acid sample is denatured at 95° C. in order to generate single stranded nucleic acid. Specific primers, as discussed below, are then annealed at 370° C. to 70° C., depending on the proportion of AT/GC in the primers. The primers are extended at 72° C. with Taq polymerase in order to generate the opposite strand to the template. These steps constitute one cycle, which may be repeated in order to amplify the selected sequence.

Primers for the amplification of a selected sequence should be selected from sequences which are highly specific and form stable duplexes with the target sequence. The primers should also be non-complementary, especially at the 3' end, should not form dimers with themselves or other primers, and should not form secondary structures or duplexes with other regions of nucleic acid. In general, primers of about 18 to 20 nucleotides are preferred, and may be easily synthesized using techniques well known in the art.

In another aspect, the present invention relates to vectors and host cells comprising the above mentioned nucleic acid sequences. The above described nucleic acid molecules which encode protein SIC (or portions thereof) may be readily introduced into a wide variety of host cells. Representative examples of such host cells include plant cells, eukaryotic cells, and prokaryotic cells. Within preferred embodiments, the nucleic acid molecules are introduced into cells from a vertebrate or warm-blooded animal, such as a human, macaque, dog, cow, horse, pig, sheep, rat, hamster, mouse, or a fish, or any hybrid thereof.

The nucleic acid molecules (or vectors) may be introduced into host cells by a wide variety of mechanisms, including for example calcium phosphate-mediated transfection (Wigler et al., Cell 14:725, 1978), lipofection; gene gun (Corsaro and Pearson, Somatic Cell Gen. 1:603, 1981; Graham and Van der Eb, Virology 52:456, 1973), electroporation (Neumann et al,. EMBO J. 1:841–845, 1982), retroviral, adenoviral, protoplast fusion-mediated transfection or DEAE-dextran mediated transfection (Ausubel et al., (eds.), Current Protocols in Molecular Biology, John Wiley and Sons, Inc., NY, N.Y., 1987).

The nucleic acid molecules, antibodies, and proteins of the present invention may be labeled or conjugatad (either through covalent or non-covalent means) to a variety of labels or other molecules, including for example, fluorescent markers, enzyme markers, toxic molecules, molecules which are nontoxic but which become toxic upon exposure to a second compound, and radionuclides.

Representative examples of fluorescent labels suitable for use within the present invcetion include, for example, Fluorescein Isothiocyanate (FITC), Rodamine, Texas Red, Luciferase and Phycoerythrin (PE). Particularly preferred for use in flow cytometry is FITC which may be conjugated to purified antibody according to the method of Keltkamp in "Conjugation of Fluorescein Isothiocyanate to Antibodies. I. Experiments on the Conditions of Conjugation," Immunology 18:865–873, 1970. (See also Keltkamp, "Conjugation of Fluoresscein Isothiocyanate to Antibodies. II. A Reproducible Method," Immunology 18:875–881, 1970; and Goding, "Conjugation of Antibodies with Fluorochromes: Modification to the Standard Methods," J. Immunol. Methods 13:215–226, 1970). For histochemical staining, HRP, which is preferred, may be conjugated to the purified antibody according to the method of Nakane and Kawaoi {"Peroxidase-Labeled Antibody: A New Method of Conjugation," J. Histochem. Cytochem. 22:1084–1091, 1974; see also, Tijssen and Kurstak, "Highly Efficient and Simple Methods for Preparation of Peroxidase and Active Peroxidase Antibody Conjugates for Enzyme Immunoassays," Anal. Biochem. 136;451–457, 1984).

Representative examples of enzyme markers or labels include alkaline phosphatase, horse radish peroxidase, and β-galactosidase. Representative examples of toxic molecules include ricin, abrin, diphtheria toxin, cholera toxin, gelonin, pokeweed antiviral proteein, tritin, Shigella toxin, and Pseudomonas exotoxin A. Representative examples of molecules which are nontoxic, but which become toxic upon exposure to a second compound include thymidine kinases such as HSVTK and VZVTK. Representative examples of radionuclides include Cu-64, Ga-67, CTa-68, Zr-89, Ru-97, Tc-99m, Rh-105, Pd-109, ln-111, I-123, I-125, I-I31, Re-186, Re-188, Au-I98, Au-199, Pb-203, At-211, Pb-212 and Bi-212.

As will be evident to one of skill in the art given the disclosure provided herein, the above described nucleic acid molecules, antibodies, proteins and peptides may also be labeled with other molecules such as colloidal gold, as well either member of a high affinity binding pair (e.g., avidin-biotin).

As noted above, the present invention also provides a variety of pharmaceutical compositions, such as vaccine compositions against certain streptococcal infections, comprising one of the above described anti-protein SIC antibodies, or protein SIC (or a peptide portion thereof), along with a pharmaceutically or physiologically acceptable carrier, excipients or diluents. Generally, such carriers should be nontoxir, to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

In addition, the pharmaceutical compositions of the present invention may be prepared for administration by a variety of different routes, including for example intraarticularly, intracranially, intradermally, intramuscularly, intraocularly, intraperitoneally, intrathecally, intravenously, subcutaneously or even directly into a tumor (for example, by stereotaxic injection). In addition, pharmaceutical compositions of the present invention may be placed within containers, along with packaging material which provides instructions regarding the use of such pharmaceutical compositions. Generally, such instructions will include a tangible expression describing the reagent concentration, as well as within certain embodiments, relative amounts of excipient ingredients or diluents {e,g., water, saline or PBS) which may be necessary to reconstitute the pharmaceutical composition.

As previously mentioned, protein SIC is involved in *S. pyogenes* pathogenicity and moreover, it is an extracellular protein. Hence, by carrying out an analysis of protein SIC, it is possible determine the presence of virulent *Streptococcus pyogenes* bacteria in a sample. Consequently, other objects of the present invention relates to methods and kits for analysis of protein SIC and/or corresponding antibodies based on for example enzyme-linked immonosorbent assy (ELISA), radioimmunological assay (RIA) and the polymerase chain reaction (PCR).

As previously mentioned, the present patent application relates to protein SIC, a novel extracellular protein of group A streptococci. Analogous to other proteins encoded by genes under control of mga, protein SIC contains repeated sequences. However, the sequence of protein SIC, including the repeats, shows no homology to previously sequenced genes. It is also noteworthy that in contrast to all other described products of the mga regulon, protein SIC does not have the typical structural features of cell wall proteins in Gram-positive bacteria; i.e. a COOH-terminal region anchored to the cell wall through an LPXTG motif (Fischetti et al., 1990: Mol. Microbiol. 4, 1603–1605; Schneewind et al., 1995: Science 268, 103–106; Schneewind et al., 1992: Cell 70, 267–281), followed further towards the COOH-terminus by a hydrophobic membrane-spanning domain and a tail of mostly positively charged amino acid residues. The missing cell wall anchor, the occurrence of a typical signal sequence, and the fact that considerable amounts of protein SIC is found in the growth medium, suggest that the molecule is secreted and has extracellular function(s).

Previous work has demonstrated several interactions between components of the complement system and proteins encoded by genes of the mga regulon. Members of the M protein family (M protein, protein Arp, protein Sir, and protein H) have been reported to bind complement factor H, CD46, and/or the C4b-binding protein (Horstmann et al., 1988: Proc. Natl. Acad. Sci. U. S. A. 85, 1657–61; Okada et al., 1995: Proc. Natl. Acad. Sci. U. S. A. 92, 2489–2493; Thern et al., 1995: J. Immunol. 154, 375–386; WO 91/19740; EP 0 371 199; EP 0 367 890), three proteins with regulatory functions in the complement system. Furthermore, the C5a peptidase (Wexler et al., 1985: Infect. Immun. 39, 239–246) which can be released from the streptococcal cell wall by a cysteine proteinase produced by the bacteria (Berge et al., 1995: J. Biol. Chem. 270, 9862–9867), cleaves the C5-derived fragment C5a and destroys its chemoattractant activity for polymorphonuclear leukocytes (Wexler et al., 1985: Proc. Natl. Acad. Sci. U. S. A. 82, 8144–8148).

The specific interactions between protein SIC and the plasma proteins clusterin and HRG resulted in a study of the final cytolytic step in the complement cascade. Clusterin is known to inhibit the hemolytic activity of complement by binding to MAC (Membrane Attack Complex) (Tschopp et al., 1993: J. Immunol. 151, 2159–2165; Tschopp et al., 1994: Clin. Exp. Immunol. 97 suppl 2, 11–14), whereas the influence of HRG on MAC is biphasic, inhibitory or stimulatory, depending on the experimental conditions (Chang et al., 1992: Blood 79, 2973–2980). As demonstrated here, protein SIC was inhibitory to hemolysis in classical pathway as well as alternative pathway systems. Furthermore, protein SIC was shown to be incorporated into C5b–C9 complexes formed in serum. Although other mechanisms may also be considered, the findings suggest that the anticomplementary action af protein SIC is focused on the terminal cytotoxic functions of complement.

The metabolically inert erythrocyte is a very sensitive target for MAC whereas most pathogenic bacteria including streptococci are resistant to complement-mediated cytolysis. However, apart from its cytolytic activity, MAC also has pro-inflammatory effects by stimulating the production and release of inflammatory mediators such as reactive oxygen metabolites, metabolites of arachidonic acid, and cytokines (Morgan 1989: Biochem. J.: 264, 1–14). Bacterial products affecting the various functions of MAC, directly or indirectly, could therefore influence the host-parasite relationship. The molecular complexity necessary to establish and maintain this relationship, makes it difficult to predict the consequences of any isolated interaction. However, in the case of pathogenic and virulent bacteria like S. pyogenes, the balance is disturbed, and there is circumstantial evidence that protein SIC may contribute to the imbalance of the host-parasite relationship in S. pyogenes infections.

To our knowledge protein SIC is the first bacterial protein reported to interact with clusterin or HRG. As mentioned, glomerulonephritis represents a medically significant sequelae following infections with S. pyogenes. In these cases certain M serotypes are more common, including the two protein SIC-producing serotypes M1 and M57 (Holm, 1988: Acta Pathol. Microbiol. Scand. 96, 189–193). In post-streptococcal glomerulonephritis immunoglobulin deposits are found in the glomeruli. Interestingly, MAC is regarded as a mediator of glomerular injury in immune complex-related disease (Couser et al., 1985: Kidney Int. 28, 879–890), and clusterin was found to be co-localized with MAC in biopsies from glomerulonephritic kidneys (French et al., 1992: Clin. Exp. Immunol. 88, 389–393).

Also, plasma depleted of clusterin (to <30%) enhanced proteinuria and deposition of MAC components in perfused kidneys (Saunders et al., 1994: Kidney Int. 45, 817–827). The association of protein SIC to nephritogenic M serotypes, and its binding of clusterin in human plasma, makes it interesting to test if protein SIC can induce kidney damage in an animal model.

Since the late 1980's a world-wide increase of hyperacute, toxic, and often lethal S. pyogenes infections, has attracted also public attention (Nowak, 1994: Science 264, 1665). These systemic infections have particularly been associated with streptococci of the M1 serotype, and the observation that all M1 strains tested, including isolates from Swedish patients with toxic and severe infections (Holm et al., 1992: J. Infect. Dis. 166, 31–37), carry and express the sic gene, supports the notion that protein SIC plays a role in pathogenicity and virulence. The present invention may therefor be used for preventing and/or treating S. pyogenes infections.

As previously mentioned, effective amounts of the protein or fragments or variants thereof can be used as active ingredients in pharmaceutical compositions, especially in vaccine compositions against streptococcal infections, possibly together with pharmaceutically acceptable adjuvants and excipients. Suitable pharmaceutically acceptable adjuvants are those conventionally used in this field. Examples of suitable excipients are mannitol, lactose, starch, cellulose, glucose, etc., only to mention a few. The examples given of the adjuvant and the excipients are not to be regarded as limiting the invention.

The invention will now be described in more detail with reference to the accompaying drawings, in which

BRIEF DESCRIPTION OF THE FIGURES

FIG. 11 shows sequence similarities between protein SIC variants from strain AP1 (SEQ ID NO: 2) and strain U1034 (SEQ ID NO: 3). Identical amino acid residues are boxed. The sequences correspond to the processed part of the proteins.

FIG. 12 describes sequence similarities between protein SIC from strain AP1 (SEQ ID NO: 2) and strain U1004 (SEQ ID NO: 4). Identical amino acid residues are boxed.

Figure 1:
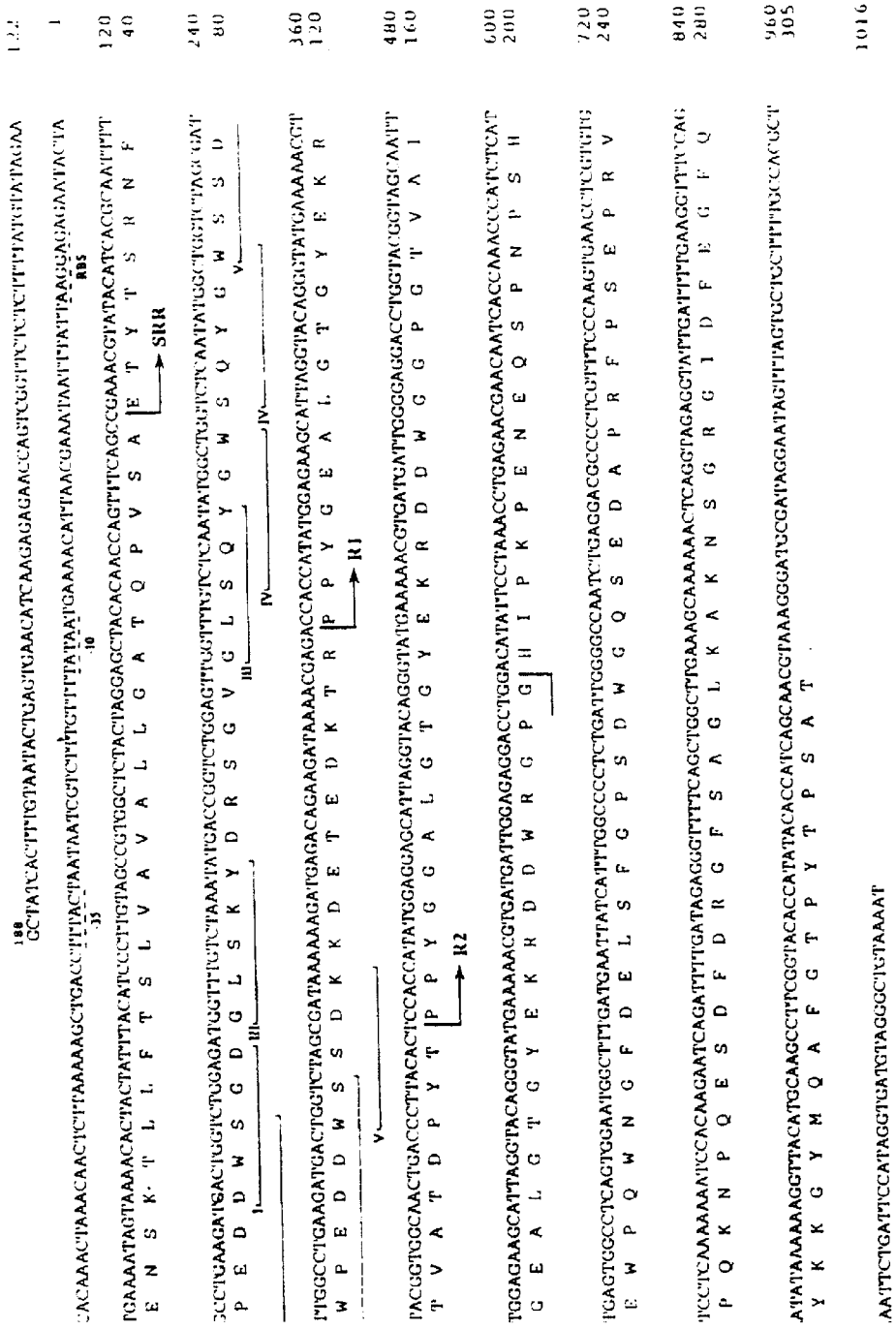
FIG. 1 shows the nucleotide sequence and deduced amino acid sequence of the sic gene from the S. pyogenes strain AP1. The first 188 nucleotides representing the sequence between the protein H gene (sph) and the sic gene, and the first 131 nucleotides of the coding sequence have been published (Gomi et al., 1990: J. Immunol. 144, 4046–4052). In this work the sequence from nucleotide 7 in the coding sequence were determined. The start of the isgnal sequence (Ss), the $NH_2$-terminal short repeat region (SRR), and the tandem repeats R1–R3 are indicated with arrows. The short repeats (I–V) are marked with bars. Possible −35 and −10 promoter sequences and the ribosomal binding site (RBS) are denoted with dashed lines.

SEQ ID NO:1 and SEQ ID NO:2, respectively, relate to the DNA sequence and the deduced amino acid sequence of a gene encoding protein SIC that has been isolated from *Streptococcus pyogenes*, strain AP1(40/58). SEQ ID NO: 3 and SEQ ID NO: 5 relate to a partial DNA sequence and a deduced amino acid sequence of a gene encoding protein SIC that has been isolated from *Streptococcus pyogenes*, strain U1034. SEQ ID NO: 4 and SEQ ID NO: 6 relate to a partial DNA sequence and a deduced amino acid sequence of a gene encoding protein SIC that has been isolated from *Streptococcus pyogenes*, strain U1004.

The invention vill now be further described with reference to the following examples. These examples are only given for the purpose of illustration and are not intended to limit the scope of the invention claimed herein.

EXAMPLES

General experimental materials and methods:
Bacterial Strains, Bacteriophage, and Plasmids
Protein SIC and the sic gene were isolated from *S. pyogenes* strain AP1 (40/58) of the M1 serotype from the Institute of Hygiene and Epidemiology, Prague, Czech Republic. Fortyeight additional strains of different M serotypes were also obtained from this Institute. These strains have been described (Ben Nasr et al., 1995: Biochem. J. 305, 173–180). *S. pyogenes* strains of serotypes M3, M33, M42, M52, M61, and M67 were kindly provided by Dr. U. Sjöbring, Lund University, and a collection of 35 M1 strains isolated in Sweden 1980–89 were kindly provided by Dr. Stig Holm, Umeå University. One *S. pyogenes* strain of serotype M1 and two of type M57 were from the late Dr. L. W. Wannamaker. The sic gene was cloned from a λEMBL3 clone previously described (Åkesson et al., 1994: Biochem. J. 300, 877–886). Plasmid vectors pUC18/19 (Yan-nisch-Perron et al., 1985: Gene 33, 103–119) and pK18/19 (Pridmore, 1987: Gene 56, 309–312) were used in subcloning experiments. PCR products were cloned into the inducible secretion vector pHD389 (Dalböge et al., 1989: Gene 79, 325–332). The *E. coli* strain JM109 was used as host for recombinant plasmids. Streptococci were grown in Todd-Hewitt broth supplement with 0,2% yeast extract and *Escherichia coli* in LB broth.

Protein and Antisera

Recombinant M1 protein (Åkesson et al., 1994: Biochem. J. 300, 877–886) and protein PAB (de Château and Björck, 1994: J. Biol. Chem. 269, 12147–12151) were purified as previously described. Human serum albumin (HSA) was from Sigma (St. Louis, Mo.). The monoclonal antibody MCaE11 directed against a neoantigen of polymerized C9 within the C5b-C9 membrane attack complex (MAC) of complement (Mollnes et al., 1985: Scand. J. Immunol. 22, 197–202) was kindly provided by Dr. T. E. Mollnes, the National Holspital, Norway. Antisera against purified streptococcal protein SIC were raised in rabbits. Sheep anti-rat clusterin (polyclonal IgG fraction) crossreacting with human clusterin was purchased from Quidel (San Diego, Calif.). Goat antisera against human histidine-rich glycoprotein was a kind gift from Dr. William T. Morgan (University of Missouri, Kansas City, Mo.). Peroxidase-conjugated goat anti-rabbit IgG (Bio-Rad, Richmond, Calif.) and donkey anti-sheep IgG (ICN, Aurora, Ohio) were used as secondary antibodies.

Purification of Clusterin and HRG

For the purification of clusterin and histidine-rich glycoprotein (HRG) fresh human plasma supplemented with 1 mM benzamidine and 0.4 mM phenylmethylsulfonyl fluoride was used. Clusterin was purified by a method modified from a previous study (Wilson and Easterbrook-Smith, 1992: Biochim. Biophys. Acta 1159, 319–326). Thus, Human plasma was differentially precipitated with polyethyleneglycol (12–23% w/v). The precipitate was then passed over an IgG-Sepharose column (Pharmacia). The column was washed with PBSA and bound proteins were eluted with 0.1 M glycine-HCl, pH 2.0. The material was dialyzed against 20 mM Tris, pH 7.5, and subjected to a Mono Q column. Using a linear NaCl gradient a protein peak eluted at 0.3 M NaCl was found to contain a single band of 80 kDa when analyzed by SDS-PAGE under non-reducing conditions. The material gave rise to a single band of 35 kDa when run under reducing conditions in the presence of 5% β-mercaptoethanol. The bands were identified as clusterin in Western blot experiments using anti-clusterin antibodies. HRG was purified using the protocol of Saigo et al (J. Biol. Chem. 264, 8249–8253 (1989)). Briefly, plasma was absorbed with CM-Sephadex (Pharmacia). The matrix was washed extensively with destilled water and adsorbed proteins were eluted with 0.5 M $NH_4HCO_3$. After dialysis against PBS the material was applied to a HiTrap Heparin column (Pharmacia). The column was washed with PBS and proteins were eluted with 1.0 M NaCl. The eluate was dialyzed against 20 mM Tris, pH 7.5, and subjected to ion-exchange chromatography on a Mono Q column. A linear NaCl gradient was used and the peak at 0.25 M NaCl was collected. The resulting preparation consisted of two major bands of 70 and 63 kDa when examined by SDS-PAGE under non-reducing conditions. The identity of the bands with HRG was confirmed by Western blotting using anti-HRG antisera.

Electrophoresis and Electroblotting

SDS-PAGE was performed as described (Neville, 1971: J. Immunol. Meth. 72, 49–59) using gels of 8% or 12% acrylamide content and 3.3% crosslinking. Before loading, samples were boiled 3.5 min in an equal volume of buffer containing 2% SDS. Samples run under reducing conditions were boiled in the presence of 5% 2-mercaptoethanol. Western blotting was performed by transferring proteins to polyvinylidene difluoride (PVDF) membranes (Immobilon, Millipore, Bedford, Mass.) as described by Towbin (Proc. Natl. Acad. Sci. U. S. A. 76, 4350–4354 (1979)). After blocking, membranes were incubated 1 h with antisera against protein SIC (1:200 v/v), HRG (1:500 v/v), or antibodies towards clusterin (5 μg/ml), followed by a peroxidase-labeled secondary antibody (1:1000 v/v). For visualization of bound antibody, membranes were incubated in 0.02% (w/v) 3-amino-9-ethylcarbazol, 0.06% (v/v) $H_2O_2$ in 50 mM sodium acetat buffer, pH 5.0.

Cloning Techniques and Sequence Determination

The PCR product amplified for the cloning of the sic gene was generated with primers containing recognition sites for NarI and XbaI, and cloned into pHD389 digested with the same enzymes. Standard cloning procedures were used (Sambrook et al., 1989: Molecular cloning: A laboratory manual, 2nd ed. Cold Spring Harbour Laboratory, Cold Spring Harbour, N.Y., USA). Restriction enzymes and T4 DNA ligase were obtained from Promega. DNA sequencing was performed with Sequenase (Pharmacia) according to the manufacturer's instructions. Ordered sets of deletions in template plasmid DNA were prepared using exonuclease BAL-31 (Promega). Computer search for sequence homology was made in the GenBank and EMBL databases. Analysis of sequence data was performed using the GeneWorks program (Intelligenetics, Mountain View, Calif., USA).

Other Methods $NH_2$-terminal amino acid sequence analysis of proteins electrotransferred to PVDF membranes were performed on an Applied Biosystems 470A gas-liquid solid phase sequenator. Clusterin, HRG, and albumin were labeled with $^{125}I$ using the Bolton and Hunter reagent (Amersham Corp. Buckinghamshire, Great Britain). The specific activities were beteween 3 and 10 μCi per μg of protein.

Example 1

Purification of Protein SIC from *Streptococcus Pyogenes,* Strain AP1

Streptococcal protein SIC was purified by growing AP1 bacteria to mid-log phase ($A_{600}$=0.5) and precipitating the culture supernatant with 30% ammonium sulfate. The resulting precipitate was resuspended to 1/100 of the starting volume with 20 mM Tris, pH 7.5, and dialyzed against the same buffer.

This material was applied to a Mono Q column on an FPLC system (Pharmacia, Uppsala, Sweden). Using a linear NaCl gradient, a single sharp peak was eluted at 0.3 NaCl. Corresponding fractions were pooled, concentrated, and subjected to gel filtration chromatography on a Superose 12 column (Pharmacia) in PBSA (0.03 M phosphate, 0.12 M NaCl, 0.02% $NaN_3$, pH 7.2). Fractions containing the suspected protein SIC were pooled and the identity of the protein was confirmed by $NH_2$-terminal amino acid sequencing and later by Western blotting using antisera against protein SIC. The yield was 0.5–2 mg purified protein SIC per liter of culture.

Recombinant protein SIC was purified from an *E. coli* strain JM109 harbouring the sic gene in pHD389. The strain was grown to mid-log phase at 30° C. before inducing protein production by raising the temperature to 40° C. for 4 hours. The culture supernatant was collected and purification of protein SIC was performed as described above. In order to examine the presence of protein SIC in other group A streptococcal strains, cultures grown to mid-logarithmic phase were precipitated with 30% ammonium sulfate, the precipitates were washed with ice cold ethanol, dissolved in 100 μl SDS-PAGE sample buffer, and subjected to Western blot analysis using rabbit antiserum against protein SIC.

Example 2

Sequencing and Location of the SIC Gene

The previously reported sequence of the protein H gene (sph) revealed the first 138 bp of an open reading frame 188 bp downstream of the stop codon for sph (Gomi et al., 1990: J. Immunol. 144, 4046–4052; EP 371 199). To determine the structure of the possible downstream gene, a phage clone, λ1:4 (Åkesson et al., 1994: Biochem. J. 300, 877–886) harbouring both the M1 gene (emm1) and sph was employed for subcloning. A 2.2 kbp SspI/EcoRI fragment of λ1:4 that contained the open reading frame except for the first six nucleotides was cloned into the vector pUC19. Sequencing of this subclone revealed that the entire open reading frame was 915 bp encoding a putative amino acid sequence of 305 residues (FIG. 1 (SEQ ID NOS. 2 and 13)).

The first 32 amino acid redidues represents a typical bacterial signal sequence including a positively charged $NH_2$-terminal region, a hydrophobic core, and a polar cleavage region. The predicted mature protein has 273 amino acid residues and a calculated molecular mass of 30.677 kDa. The most characteristic feature of the sequence is a central repeat region consisting of three tandem repeats of 29, 29, och 21 amino acid residues each (R1–R3), showing 90–95% internal homology.

The sequence preceding the R repeats also contains repeats although these are only five or nine amino acids long. In FIG. 1 five different repeats in this short repeat region (SRR) are indicated. They appear only twice each, and except for repeat IV they are not in tandem. Instead some of the repeats are overlapping. The sequence located COOH-terminal of the R repeats is characterized by a high proline content and in a short stretch (residue 200–220) the prolines are evenly spaced every third or fourth residue.

Computer-assisted analysis of the sequence predicted the protein to be highly hydrophilic with a pI of 4.2. A thorough search of the data bases with the entire sequence, or fragments of the sequence including all kinds of repeats, did not reveal any obvious homology either at the nucleotide or the amino acid level.

Figure 2:
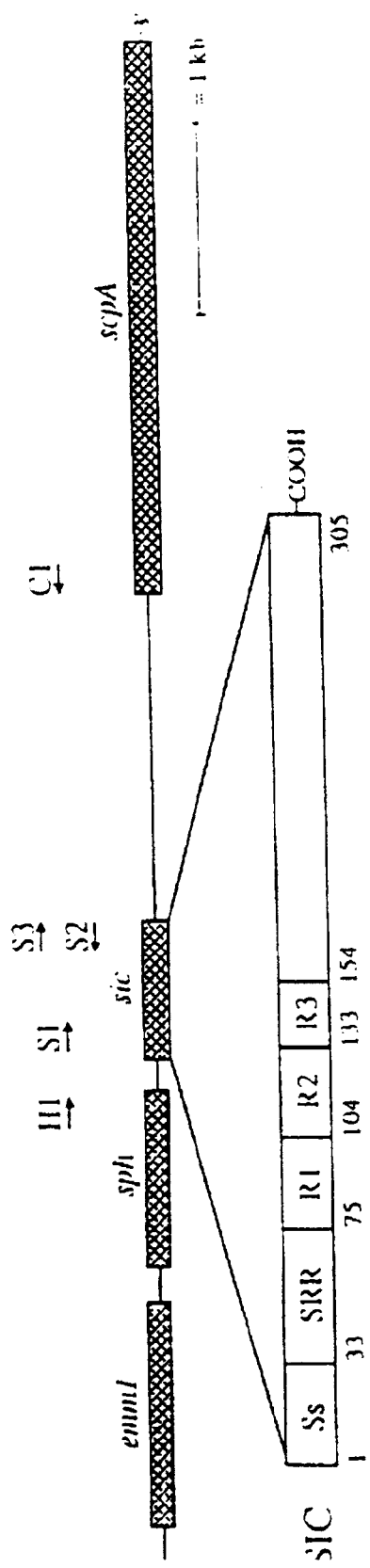
FIG. 2 discloses a map of the vir regulon of the strain AP1 and a schematic outline of the structure of protein SIC. The part of the streptococcal chromosome containing the genes of the mga locus is depicted in the upper part of the figure. The relative location and size of the genes were determined by nucleotide sequencing and PCR (Gomi et al., 1990: supra; EP 371 199; Åkesson et al., 1994: Biochem. J. 300, 877–886). The location of oligonucleotide primers used for the PCR experiments in this work are marked with arrows. In the lower part of the figure protein SIC and its domains are shown. Numbers below the schematic representation correspond to the first amino acids of the regions.

The presence of sic in the mga locus of the AP1 strain was further demonstrated by PCR of chromosomal DNA with two sets of primers (FIG. 2). A reaction with the H1 primer corresponding to the sequence of M-like genes encoding the consensus membrane-anchoring motif (Fischetti et al., 1990: Mol. Microbiol. 4, 1603–1605) and the S2 primer corresponding to the 3' end of sic generated a fragment of 1.2 kbp. This confirms the intergenic distance of 188 bp between sph and sic as determined by sequencing.

The PCR performed with the S3 primer from the 3' end of sic and the C1 primer corresponding to a part of the signal sequence of the C5a peptidase gene (scpA) generated a 2.2 kbp product. These experiments demonstrate that sic is located 188 bp downstream of sph and approximately 2.1 kbp upstream of scpA (FIG. 2).

Example 3

Cloning and Expression of Protein SIC in *E. coli* and Purification of the Protein from Streptococcal Culture Medium Oligonucleotides were constructed from the SIC sequence to generate a PCR fragment corresponding to the mature protein. This fragment was amplified by PCR using Taq DNA polymerase (Promega, Madison, Wis.). For amplification of the sic gene for cloning, primers S1 and S2 containing recognition sites NarI and XbaI respectively (FIG. 2), corresponding to base pairs (bp)97–123 and bp 928–905 of the sic sequence (FIG. 1, SEQ ID NO: 1), were used.

To investigate the occurrence of sic in other group A streptococcal isolates, PCR was performed with the S1 and S2 primer with an annealing temperature at 20° C. below the $T_m$ of the shortest primer (46° C.). Templates for the reactions were prepared by resuspending a single bacterial colony In 100 µl water, vortexing the sample vigorously, and the boiling it for 5 min. Cell debris was removed by centrifugation and 5 µl of the resulting supernatant were used in a 50 µl reaction. In order to determine the relationship of sic to other genes of the streptococcal mga locus, PCR's with two different primer pairs outlined in FIG. 2 were performed. In one reaction the H1 primer corresponding to the conserved membrane anchoring motif of cell wall proteins of Gram-positive cocci; bp 1357–1381 of the sph sequence (Gomi et al., 1990: supra; EP 371 199), and the S2 primer corresponding to the end of the sic sequence were used. In another reaction the S3 primer corresponding to bp 871–890 of the sic sequence (FIG. 1) and the C1 primer from the signal sequence of th C5a peptidase gene; bp 888–868 in the scpA sequence (Chen and Cleary, 1990: J. Biol. Chem. 265, 3161–3167), were used. Reactions were performed with AP1 chromosomal DNA as the template.

Figure 3:
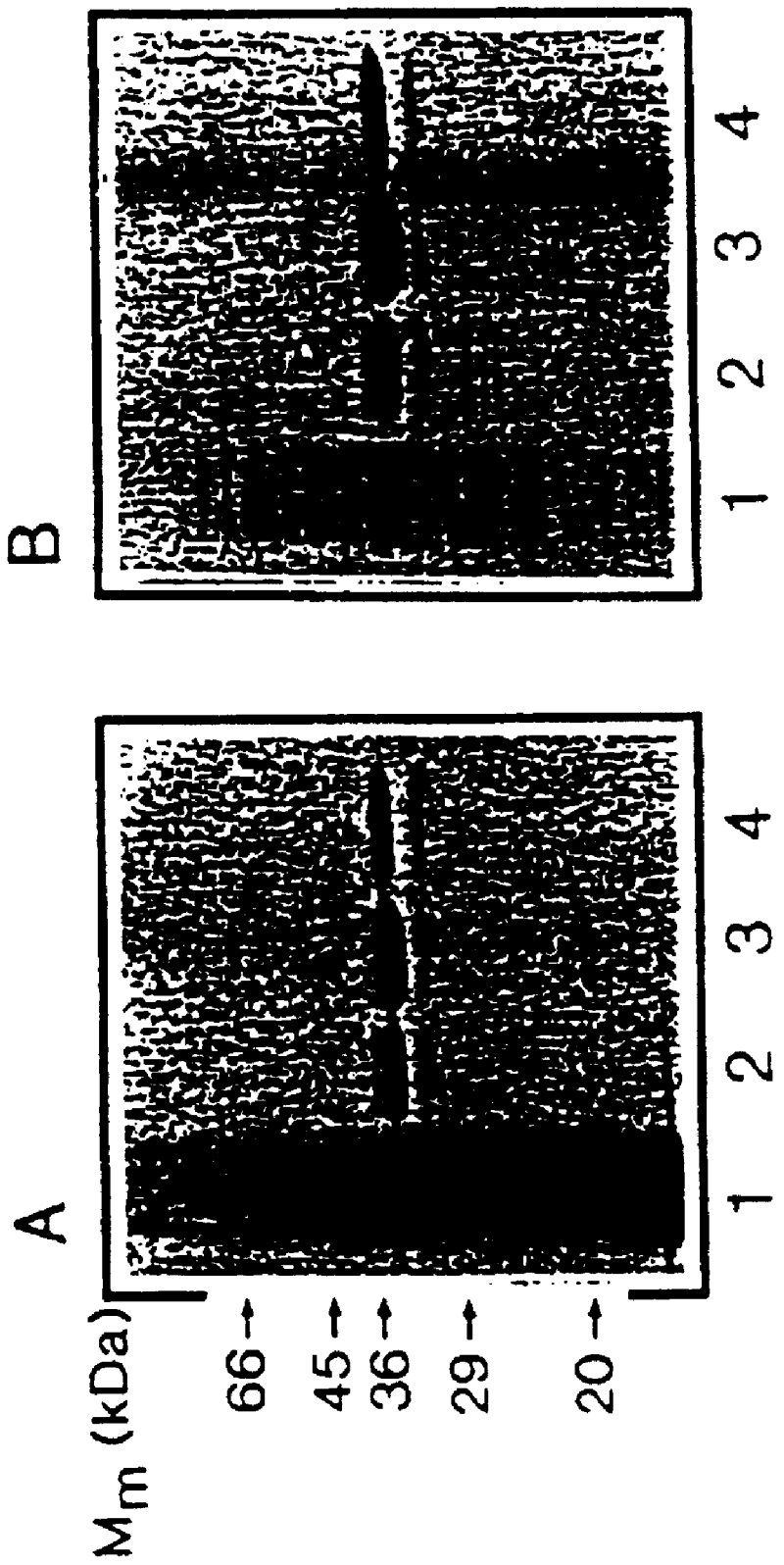
FIG. 3 relates to SDS-PAGE (sodium dodecylsulfate-polyacrylamide gel electrophoresis) analysis of protein SIC after consecutive purification steps. The purification of the wild-type protein SIC from S. pyogenes is shown in A and the purification of the recombinant protein from E. coli is shown in B. The material in lanes 1 was precipitated from culture medium with 80% ammonium sulfate followed by precipitation with 30% ammonium sulfate (lanes 2). Lanes 3 show protein SIC after an additional purification step on MonoQ, whereas the final product (lanes 4) was obatined after gel filtration on a Superose 12 column. Molecular mass markers are indicated.

The amplified fragment was cloned into the inducible expression vector pHD389. After growing the clone and inducing expression, a periplasmic lysate was examined by SDS-PAGE which showed the overexpression of a 34 kDa protein as compared to the host *E. coli* strain. Even higher amounts of the 34 kDa product was detected when analyzing the culture media after precipitation with 80% ammonium sulfate. The protein was purified using precipitation of the culture media with 30% ammonium sulfate, ion-exchange chromatography and gel filtration (FIG. 3B). The purified product was seen as a single band on SDS-PAGE and the yield was about 5 mg purified protein per liter culture.

Both the presence of a signal sequence and the absence of cell-wall anchoring or membrane-spanning sequences in the gene, suggested that the protein is secreted by streptococci of the AP1 strain. Consequently, a similar purification scheme as used for the recombinant protein was applied to the culture medium of streptococcal AP1 bacteria, and a protein with identical migration on SDS-PAGE was obtained (FIG. 3A). The estimated amount of protein SIC in a 1 liter culture was 10–15 mg from which 1–2 mg purified protein was obtained. $NH_2$-terminal amino acid analysis of the protein showed that the first five amino acids (ETYTS; SEQ ID NO:14) were identical to the start of the mature protein as indicated by the nucleotide sequence. Thus, the gene product of sic was shown to be expressed by the AP1 strain as an extracellular protein.

Example 4

Absorption of Plasma Proteins with Immobilized Protein SIC

Being a secreted product protein SIC is most likely active outside the bacterial cell. On the streptococcal chromosome protein SIC is found in a locus encoding proteins which interact with host molecules, particularly plasma proteins. In order to examine if protein SIC also has affinity for plasma proteins, fresh human plasma was mixed with the protease inhibitors benzamidine iodocetic acid to final concentrations of 5 mM each. 5 ml of undiluted plasma was immediately added to 1 mg protein SIC coupled to Sepharose. After end to end rotation for 4 hours at room temperature the protein SIC-Sepharose was extensively washed with PBS (200 times the column volume) and the proteins bound to the column were eluted with 0.1 M glycine-HCl, pH 2.0. As a control 5 ml plasma was simultaneously absorbed with glycine-Sepharose. pH was adjusted to 7.5 by adding 1 M Tris, and the eluates were concentrated about 100 fold.

Figure 4:
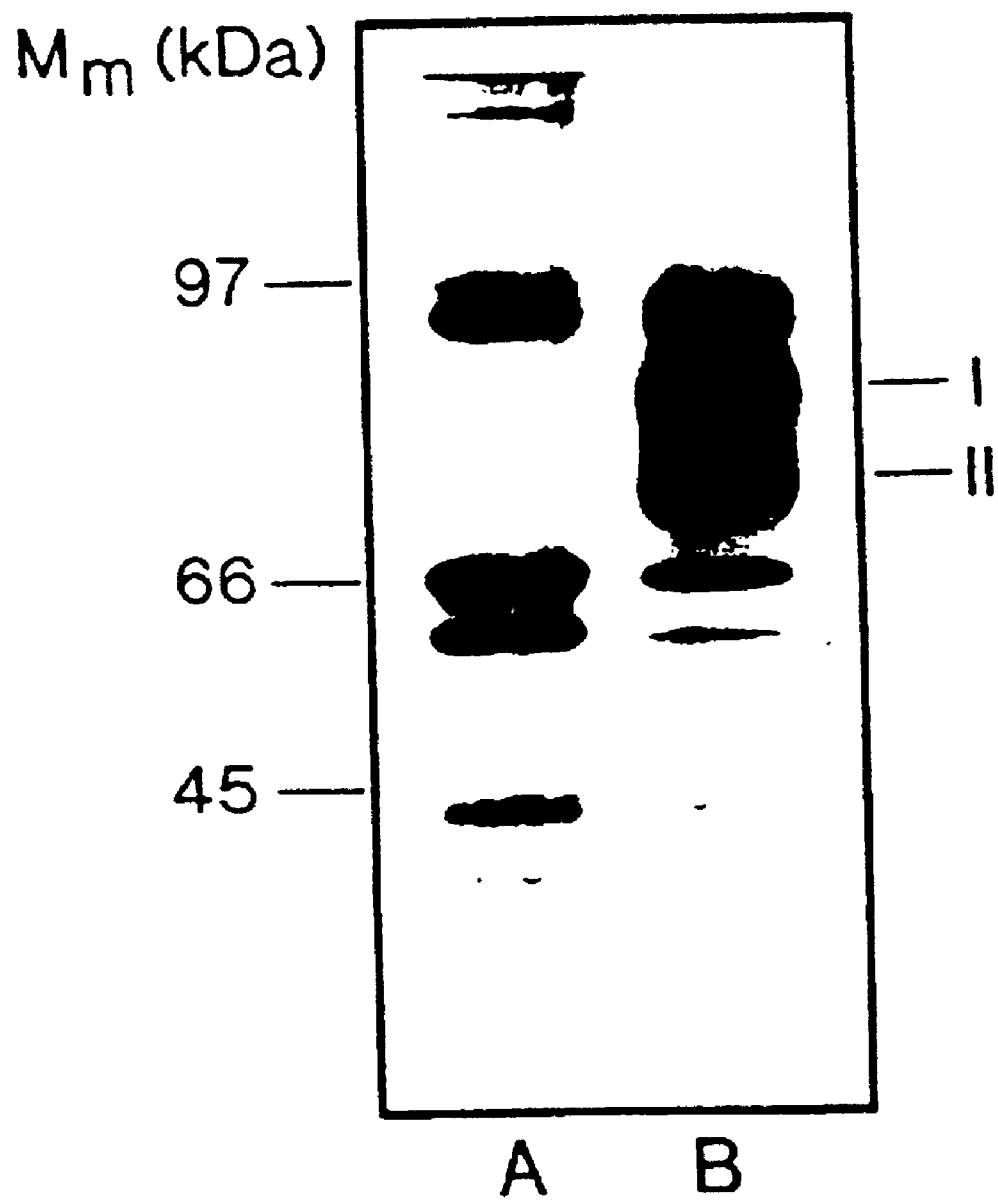
FIG. 4 shows SDS-PAGE analysis of proteins eluted from protein SIC-Sepharose after plasma absorption. Proteins eluted from glycine-Sepharose (lane A) or protein SIC-Sepharose (lane B) following incubation with human plasma. The samples were separated by SDS-PAGE (8%) under non-reducing conditions. Molecular mass markers are shown to the left. The bands of 80 kDa and 70 kDa in lane B are indicated with I and II, respectively.

The eluted material was lyophilized, resuspended in PBS at fifty times concentration and exmined on SDS-PAGE. As seen in FIG. 4, two additional bands appeared as compared to the background pattern obtained after absorption with glycine-Sepharose. The bands were electroblotted onto a PVDF-membrane, excised from the membrane, and subjected to $NH_2$-terminal amino acid sequencing.

The band of 80 kDa (labelled I in FIG. 4) showed the presence of two residues in equimolar yields after each sequencing cycle. The two sequences (DQTVSDNELQ and SLMPFSPYEP; SEQ ID NOS. 15 and 16 respectively) were identical to the $NH_2$-terminal sequences of the α and β chains of the plasma protein clusterin (Jenne et al., 1989: Proc. Natl. Acad. Sci. USA 86, 7123–7127; Kirszbaum et al., 1989: EMBO J. 8, 711–718).

The band of 70 kDa (labelled II in FIG. 4) had the sequence VSPTDCSAVE; SEQ ID NO: 17 , identifying the protein as histindine-rich glycoprotein (HRG)(Koide et al., 1986: Biochemistry 25, 2220–2225). The absorption experiments were performed with both recombinant and streptococcal protein SIC coupled to Sepharose and the same results were obtained.

Example 5

Further Analysis of the Interaction between Protein SIC and the Plasma Proteins Clusterin and Histidine-rich Glycoprotein The binding of protein SIC to clusterin and HRG was now further analyzed. Firstly, clusterin and HRG were purified from human plasma. The observations made with human plasma were then re-examined by affinity chromatography of radiolabeled clusterin and HRG on protein SIC-Sepharose. Purified radiolabeled clusterin, HRG, or HSA ($4 \times 10^5$ cpm in 1.0 ml PBS) were run on columns of Sepharose coupled with protein SIC, M1 protein, HSA. After washing with PBS bound proteins were eluted with 0.1 M glycine-HCl, pH 2.0 and the radioactivity in the fractions measured in a gammacounter.

Figure 5:
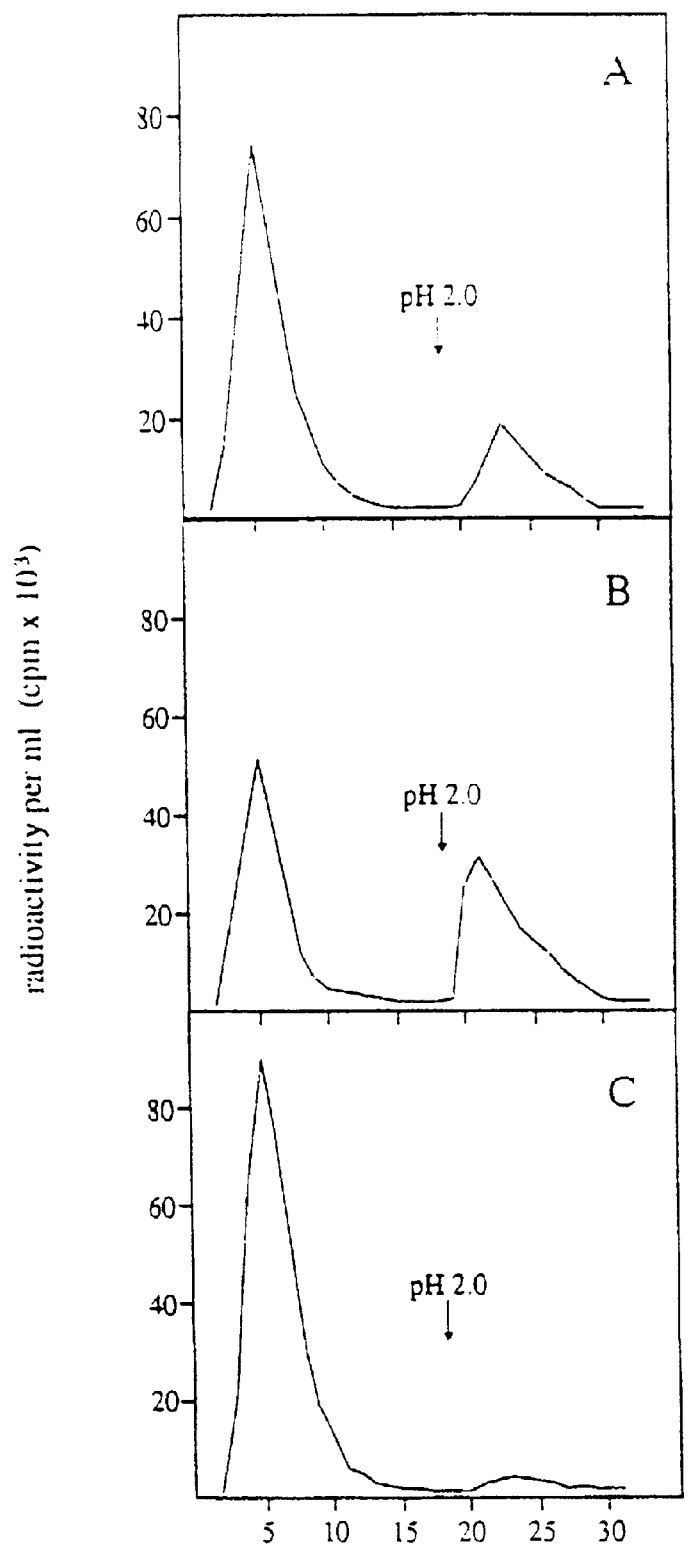
FIG. 5 discloses affinity chromatography of radiolabeled proteins on protein SIC-Sepharose. $4 \times 10^5$ cpm in 1.0 ml PBS (Phosphate Buffered Saline) of clusterin (A), HRG (B), or albumin (C) was applied to a protein SIC-Sepharose column. After washing with the application buffer proteins bound to on the column were eluted with 0.1 M glycine, pH 2.0. The radioactivity of the fractions were determined.

About 30% of the $^{125}$I-clusterin and about 60% of the $^{125}$I-HRG were retained after chromatography on a protein SIC-Sepharose column. In contrast, less than 5% of iodine labeled albumin was eluted from the column (FIG. 5). Additionally, less than 5% of $^{125}$I-clusterin or $^{125}$I-HRG were bound to columns of M1 protein or HSA-Sepharose (data not shown).

The interactions were also tested by indirect ELISA (Engvall and Perlmann, 1971: Immunochemistry 8, 871–874), which analysis was performed by coating microtiter plates (Maxisorb, NUNC, Denmark) over night at 4° C. with serial dilutions of protein SIC (starting concentration 2 μg/ml). The plates were washed in PBST and incubated with clusterin (5 μg/ml in PBST containing 2% bovine serum albumin) or HRG (1.25 μg/ml) diluted in PBST containing 1% gelatin (PBSTG). Bound proteins were detected by purified antibodies to clusterin (10 μg/ml) or antisera against HRG (1:2000 v/v), and binding was visualized by a horseradish peroxidase-conjugated secondary anti-body against rabbit or sheep IgG (1:5000 v/v). All incubations were done at 37° C. for 1 h and followed by a washing step. Substrate solution, 0.1% (w/v) diammonium-2,2-azino-bis-(3-ethyl-2, 3-dihydrobenzthiazoline)-6-sulfonate (ABTS), 0.012% (v/v) $H_2O_2$ in 100 mM citric acid, 100 mM $NaH_2PO_4$, pH 4.5, was added and the change in absorbance at 405 nm was determined after 30 min.

A competitive ELISA was performed using the same procedure specified above except for the following: microtiter plates coated with either clusterin (1.5 μg/ml) or HRG (0.5 μg/ml) were incubated with a mixture of protein SIC (2 μg/ml for binding to clusterin; 1 μg/ml for binding to HRG) and serial dilutions of the competitor protein (starting concentration 20 μg/ml). Bound protein SIC was detected by a specific rabbit antisera (1:1000 v/v) followed by a secondary antibody towards rabbit IgG (1:3000 v/v) and ABTS/$H_2O_2$.

Figure 6:
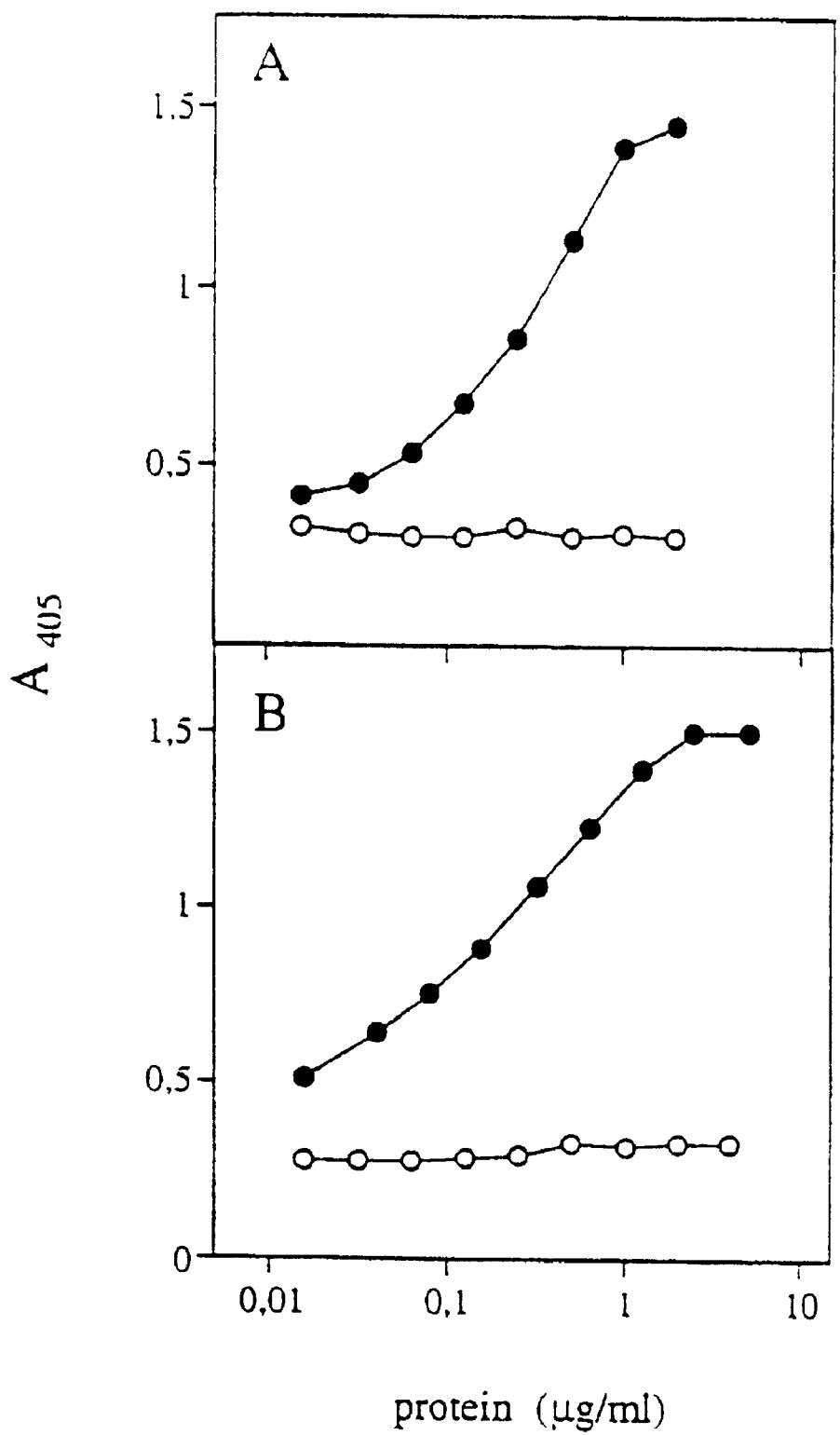
FIG. 6 shows binding of clusterin and HRG to protein SIC in indirect ELISA. Microtiter plates were coated with dilution series of protein SIC (●) or protein PAB (○). 5 µg/ml clusterin (A) or 1.25 µg/ml HRG (B) were applied followed by specific antibodies to these proteins and a peroxidase-labeled labeled secondary antibody. The absorption at 405 nm is presented in arbitrary units.
Figure 7:
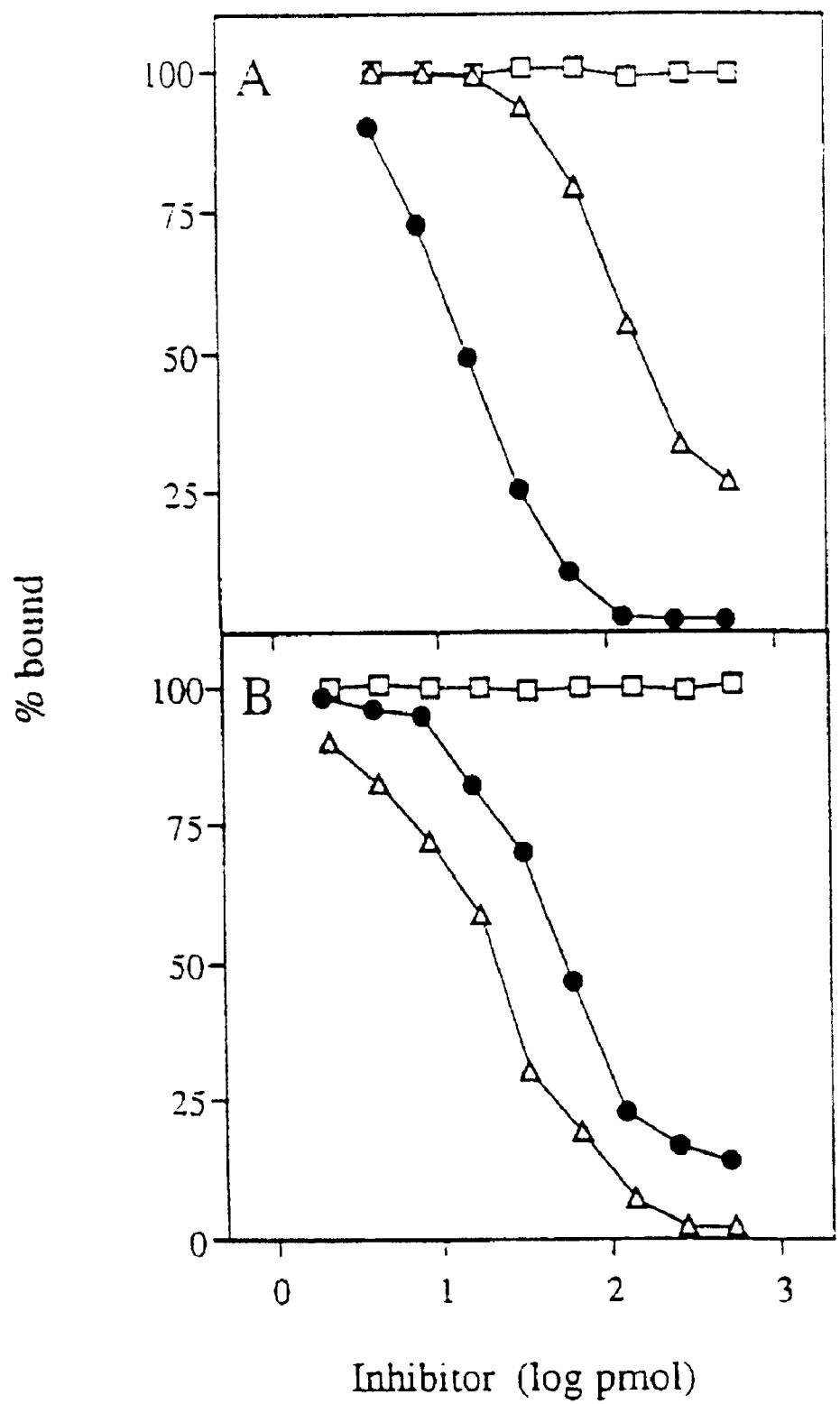
FIG. 7 relates to competition for the binding of protein SIC to clusterin and HRG. Competitive ELISAs were performed on microtiter plates coated with 1.5 µg/ml of clusterin (A) or 0.5 µg/ml of HRG (B). Dilutions of clusterin (+), HRG (Δ), or HSA (□) were mixed with an equivolume (100 µl) of protein SIC (2 µg/ml in panel A and 1 µg/ml in panel B), and the mixtures were applied to the walls of the titer plates. Protein SIC bound to the immobilized proteins was detected with specific rabbit polyclonal antiserum followed by a peroxidase-labeled secondary antibody. The results are expressed as percent of protein SIC bound in the presence of a competitor relative to the specific binding in the absence of a competitor (100%).

The results of the indirect ELISAs show that the binding of clusterin or HRG to protein SIC is concentration-dependent (FIG. 6). Additionally, competitive ELISAs with clusterin or HRG as the coated proteins and protein SIC as the probe were performed. In these experiments the binding of protein SIC to clusterin was blocked by protein by HRG although less efficient than by clusterin itself (FIG. 7A). Similarly, the binding of protein SIC to HRG was inhibited by clusterin (FIG. 7B). The results indicate overlapping or closely located binding sites for the two plasma proteins in protein SIC.

Example 6

Inhibition of Complement-mediated Hemolytic Activity by Protein SIC

Together with vitronectin, clusterin and HRG bind to the C5b-C9 complex in serum and thereby regulate the cytotoxic action of MAC (Tschopp et al., 1993: supra; Chang et al., 1992: supra). Clusterin partly inhibits hemolysis, while HRG modulates complement function in a biphasic fashion. A possible role for protein SIC in classical pathway-mediated hemolysis was assessed by the results of complement-mediated hemolytic assays and binding experiments.

Complement-mediated hemolytic assays in free solution were performed essentially as reported (Nilsson and Nilsson, 1984: J. Immunol. Meth. 72, 49–59) with tatget cells added in excess. Sheep erythrocytes, treated with rabbit antibody (NBL, Stockholm, Sweden) to yield optimally sensitized cells (EA cells), were used to measure the function of the classical pathway function. Assays were performed with veronal buffered saline (VBS) containing 0.15 mM $Ca^{2+}$ and 0.5 $Mg^{2+}$.

Alternative pathway-mediated hemolysis of guinea-pig erythrocytes (GpE) was performed in VBS containing EGTA at a final concentration of 16 mM and $Mg^{2+}$ at 4 mM. Various quantities of protein SIC were added to human serum diluted to a concentration causing 10% lysis of erythrocytes. After incubation for 30 min at room temperature EA or GpE were added at a concentration of $5 \times 10^9$ cells per ml and the mixture was incubated at 37° C. for 20 min. The reaction was stopped by adding a fifteen-fold volume of cold VBS containing 10 mM EDTA.

After centrifugation hemolysis was measured as the absorbance of the supernatant at 541 nm. The final human serum dilutions were 1:40 for assays of the classical pathway and 1:20 for the alternative pathway. The serum used was free from anti-bodies towards protein SIC. Complement-mediated hemolysis in gel was studied according to the procedure previously described (Truedsson et al., 1981: Acta Pathol. Microbiol. Scand., C. Immunol. 89, 161–166) using EA or GpE in agarose as target cells. 5 μl undiluted human serum and 1.5 μg (in 5 μl) protein SIC or protein PAB were applied to adjacent wells in the gels with a distance of 2–4 mm. Additionally, 1.5 μg bacterial proteins were added after 2, 4, 6, and 8 h incubation. After incubation of the gels at 40° C. for 16 h lysis was induced at 37° C. for 3h.

Figure 8:
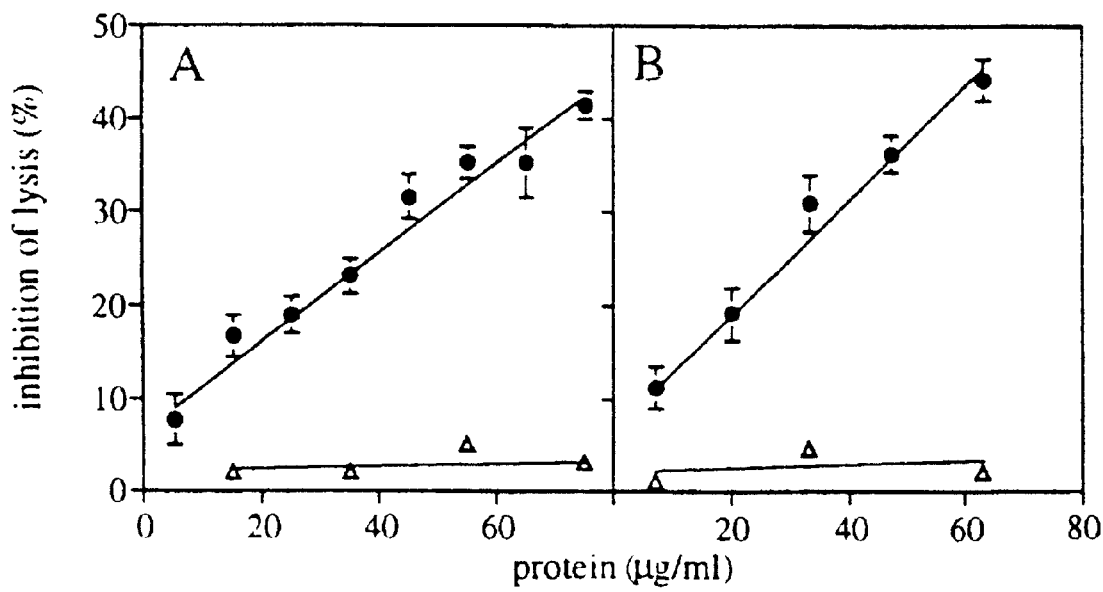
FIG. 8 shows inhibition of complement-mediated hemolysis. Diluted human serum was incubated with various concentrations of protein SIC (●) or protein PAB (-Δ-) followed by addition of sensitized sheep erythrocytes (A) or guinea-pig erythrocytes (B). Hemolysis was measured by determining the absorbance of the supernatant at 541 nm. The inhibition of lysis by the proteins was calculated by dividing the absorbance with the value obtained when incubating serum with buffer (PBS). Data represents the mean from three separate experiments and +/−SEM is indicated. In panel C, 5 µl undiluted human serum was applied to wells in agarose gels containing sensitized sheep erythrocytes (I) or guinea-pig erythrocytes (II). Protein SIC or protein PAB were applied (6 µg) in the adjacent wells as indicated. Gels were incubated at 4° C. over night and hemolysis was induced by incubation at 37° C. for 3 h.
Figure 8:
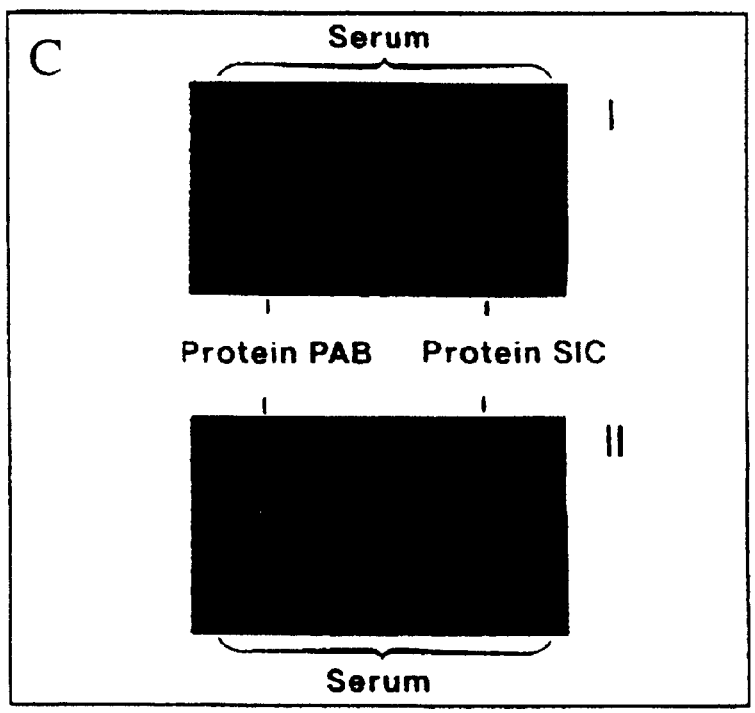

A dose dependent inhibition of complement hemolysis was obtained (FIG. 8A). To exclude non-specific degradation of complement components during the preincubation of serum an unrelated bacterial protein, the albumin-binding protein PAB of *Peptostreptococcus magnus* (de Château and Björck, 1994: supra), was used as negative control. The effect of protein SIC on the alternative pathway of complement was examined using guinea pig erythrocytes as target cells in serum chelated with EGTA and supplemented with $Mg^{2+}$.

As shown in FIG. 8B the effect of protein SIC on hemolysis of GpE was comparable to the effect on hemolysis of EA, consistent with interference at the C5b-C9 level. Similar results were obtained when effects of protein SIC were studied in hemolytic gels with EA and GpE as target cells (FIG. 8C). When protein SIC was applied adjacent to wells containing serum, the zone of lysis caused by serum was partly eclipsed. In contrast, protein PAB had no inhibitory effect on hemolysis.

The interaction between protein SIC and the terminal complement proteins in serum was examined with a capture ELISA modified from Mollnes et al., 1985: Scand. J. Immunol. 22, 183–202. Microtiter plates were coated with 1.0 μg/ml of MCaE11, a monoclonal antibody against a neoantigen of polymerized C9 that is formed during the assembly of the C5b-C9 complex. Incubation of serum gives a high level of such complexes binding to the antibody due to spontaneous in vivo activation of complement (Mollnes et al., 1985: supra). Serum diluted 1/50 in PBSTG was added to the wells followed by serial dilutions of protein SIC or SCP (starting concentrations 10 μg/ml), and the plates were incubated for 3 h at room temperature. Diluted serum was also preincubated with protein SIC or SCP at various concentrations for 3 h, after which generation of C5b-C9 complexes were stopped by addition of EDTA at 10 mM. The incubation mixtures were then transferred to antibody-coated microtiter plates for analysis. Detection of protein SIC and SCP were performed as described in example 5 using specific rabbit antisera diluted 1/1000.

Figure 9:
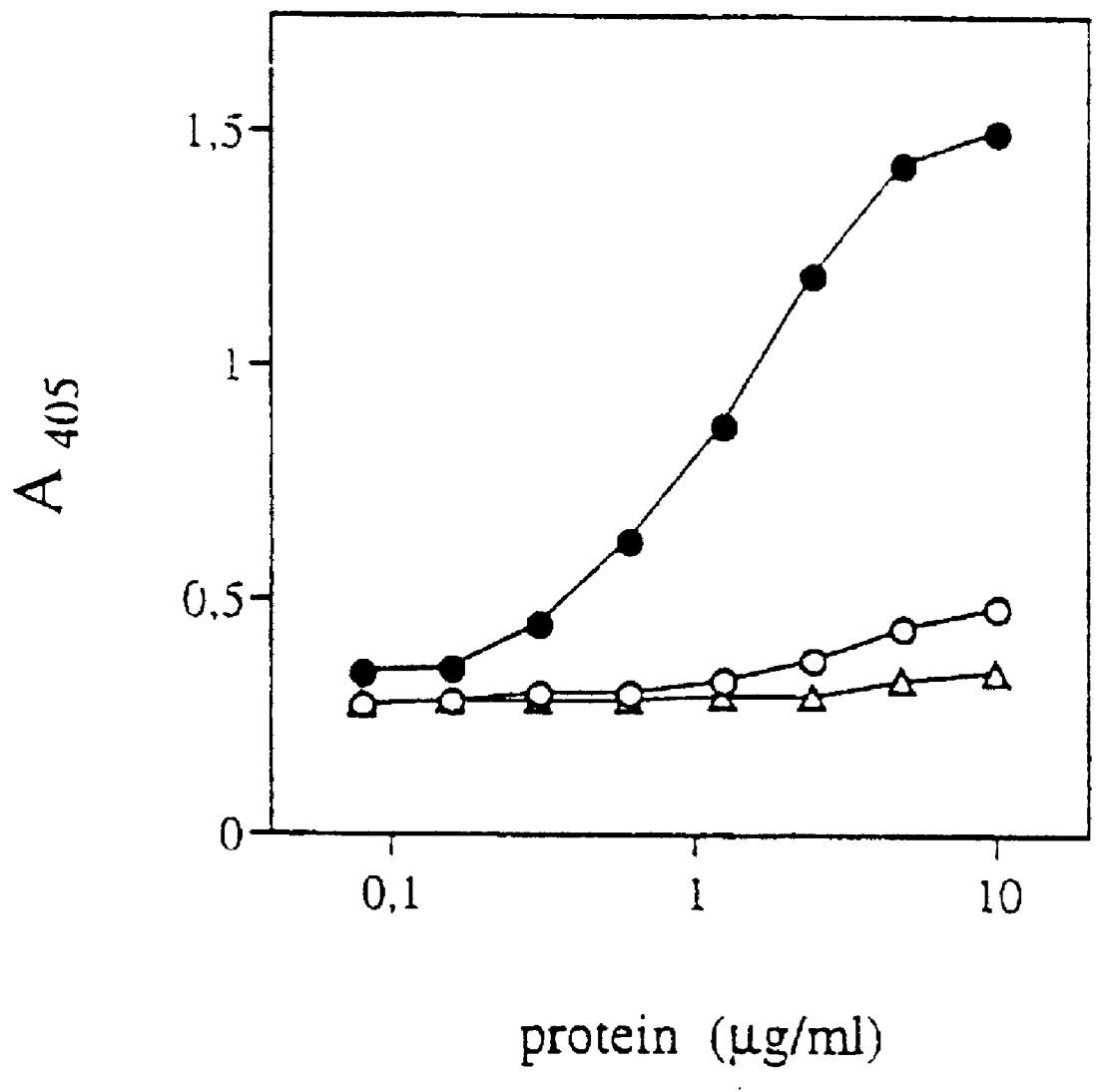
FIG. 9 relates to binding of protein SIC to C5b-C9 complexes. A monoclonal antibody directed against a neoantigen of polymerized C9 within C5b-C9 was used to coat microtiter plates (1 µg/ml). Dilution series of protein SIC (●) or SCP (Δ) were mixed with human serum in a final dilution of 1:50, and applied to the wells. Incubation was also done with a dilution series of protein SIC in buffer (○). Protein SIC and SCP were detected by specific antibodies to these proteins and a peroxidase-labeled secondary antibody.

In FIG. 9, an experiment is shown where serum and protein SIC simultaneously were added to and incubated with the solid-phase-bound antibody. The amount of bound protein SIC was then measured. In contrast to the control protein, SCP, protein SIC is incorporated into the C5b-C9 complex generated in serum. No protein SIC binding was detected in the absence of serum or in serum containing EDTA. Further experiments were carried out to ensure that deposition of complement proteins due to activation by the immunoglobulin-coated microtiter plates (Zwirner et al., 1989: J. Immunol. Meth. 124, 121–129) did not influence the results. Thus, serum was preincubated with protein SIC. After 3h EDTA was added and the incubation mixtures were transferred to the antibody-coated plates for analysis. The results obtained were virtually identical to those shown in FIG. 9.

Example 7

Distribution of Protein SIC in Strains of *S. pyogenes*

A collection of 55 group A streptococcal strains of different M types were tested for the presence of the sic gene and the expression of protein SIC. At the DNA level sic was identified by PCR using primers from the start of the coding sequence and the repeat regions and by performing the reaction under low stringency conditions. The expression of protein SIC was tested by growing the strains to mid-logarithmic phase, precipitating the culture media with 30% ammonium sulfate, and examining the precipitate in a Western blot using polyclonal antisera against protein SIC. The strains of M type 1 and 57 were positive both in the PCR and in Western blot experiments. The rest of the strains gave no PCR products and were negative in the Western blot analyses. After the initial screening, 35 additional M type 1 isolates and two M 57 strains were tested. All of these strains contained sic and expressed protein SIC. The results suggest that the sic gene is highly restricted among various M serotypes, whereas within these serotypes all isolates have and express the gene.

Example 8

Detection of Antibodies Towards Protein SIC

An indirect ELISA was performed by coating microtiter plates (Maxisorb, NUNC) over night at +4° C. with 5µg/ml protein SIC or 5 µg/ml fibrinogen (negative control). The plates were washed with phosphate buffered saline containing 0.25% Tween, and incubated for 1 h at 37° C. with two-fold dilutions of serum from two patients (starting dilution of serum was 1:10).

Patient A is infected by a virulent *Streptococcus pyogenes* strain and patient B is infected by a lesser virulent strain. Bound antibodies were detected by peroxidase-labelled antibodies towards human K light chain (DAKO). Substrate solution, 0.1w (W/v) diammonium-2,2-azino-bis-(3-ethyl-2,3-dihydro-benzthiazoline)-6-sulfonate (ABTS), 0.012% (v/v) $H_2O_2$ in 100 mM citric acid, 100 mM $NaH_2PO_4$, pH 4.5, was added and the change in absorbance at 405 nm was determined after 30 min.

Figure 10:
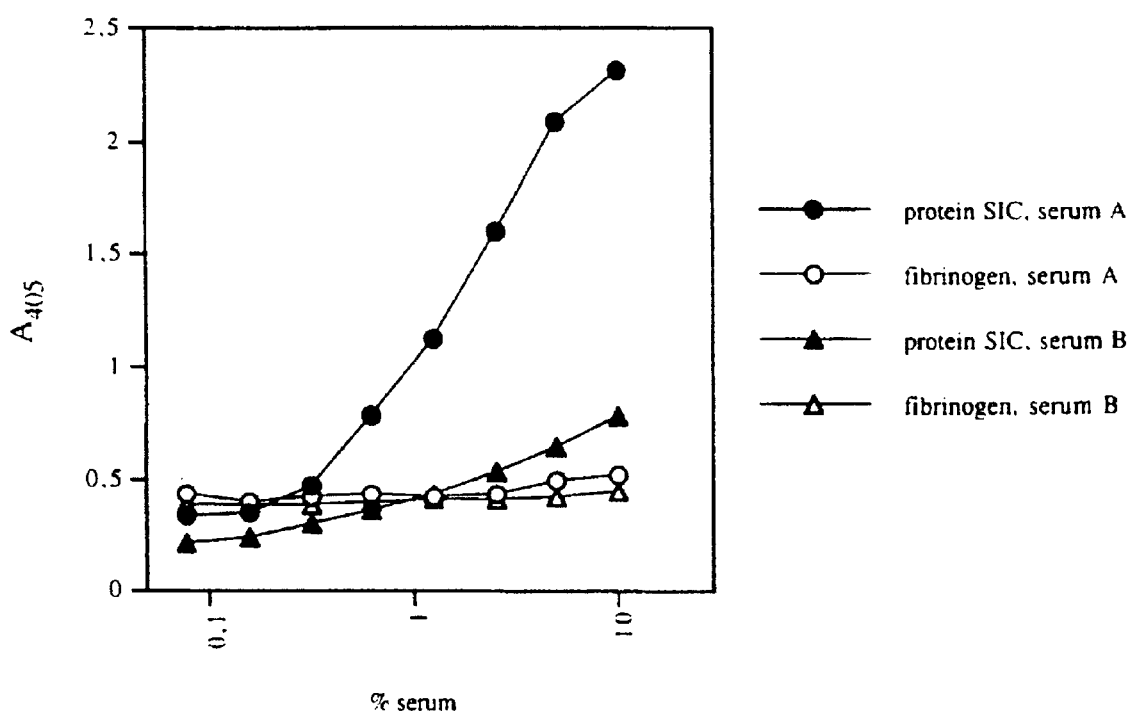
FIG. 10 relates to an ELISA assay for detecting antibodies towards protein SIC in serum. The figure clearly shows that serum A contains antibodies towards protein SIC.

The results are shown in FIG. 10. Antibodies in the serum of patient A are reacting with the coated protein SIC in a concentration-dependent manner, whereas the sera from patient B does not react with protein SIC. There is no reactivity with coated fibrinogen in either sera. Thus, only patient A has specific protein SIC-antibodies.

Example 9

Variations in the Gene Encoding Protein SIC

PCR experiments were performed using genomic DNA isolated from 35 different M type 1 strains and 2 M type 57 strains, and oligonucleotides from the 5' and 3' end of the coding sequence of sic. The size of the products from most strains were 830 bp, the same size as of the sic gene originally isolated (strain AP1, SEQ ID NO: 1). However, in 6 of the strains, sic was approximately 100 bp bigger, and in one strain 100 bp smaller. Four of the PCR-amplified products were subjected to DNA sequencing, including one bigger and one smaller sic gene. These results, which partially are disclosed in FIG. 11 (SEQ ID NOS. 18 and 3) and FIG. 12 (SEQ ID NOS. 19 and 18) respectively, show that although most parts of the sequences are conserved, there are regions with limited sequence variations. Additionally, deletions and duplication of the R repeats were detected. Protein SIC variants encoded by the four sequenced genes were isolated from the corresponding *S. pyogenes* strains. These were shown to have similar protein binding properties as protein SIC isolated from AP1.

What is claimed is:

1. An isolated protein comprising the amino acid sequence of SEQ ID NO:2.

\* \* \* \* \*

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 927 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO

-continued (iv) ANTI-SENSE: NO (vi) ORIGINAL SOURCE:
    (A) ORGANISM: Streptococcus pyogenes
    (B) STRAIN: AP1(40/58), M1 serotype (xi) SEQUENCE DESCRIPTION: SEQ ID NO:1:

```
CTCTTCGAAA TGAATATTAG AAATAAGATT GAAAATAGTA AAACACTACT ATTTACATCC      60

CTTGTAGCCG TGGCTCTACT AGGAGCTACA CAACCAGTTT CAGCCGAAAC GTATACATCA     120

CGCAATTTTG ACTGGTCTGG AGATGACTGG CCTGAAGATG ACTGGTCTGG AGATGGTTTG     180

TCTAAATATG ACCGGTCTGG AGTTGGTTTG TCTCAATATG GCTGGTCTCA ATATGGCTGG     240

TCTAGCGATA AGAAGAATG GCCTGAAGAT TGGCCTGAAG ATGACTGGTC TAGCGATAAA      300

AAAGATGAGA CAGAAGATAA AACGAGACCA CCATATGGAG AAGCATTAGG TACAGGGTAT     360

GAAAACGTG ATGATTGGGG AGGACCTGGT ACGGTGGCAA CTGACCCTTA CACTCCACCA      420

TATGGAGGAG CATTAGGTAC AGGGTATGAA AAACGTGATG ATTGGGGAGG ACCTGGTACG     480

GTAGCAATTG ACCCTTACAC TCCACCATAT GGAGAAGCAT TAGGTACAGG GTATGAAAAA     540

CGTGATGATT GGAGAGGACC TGGACATATT CCTAAACCTG AGAACGAACA ATCACCAAAC     600

CCATCTCATA TTCCTGAACC TCCTCAGATT GAGTGGCCTC AGTGGAATGG CTTTGATGAA     660

TTATCATTTG GCCCCTCTGA TTGGGGCCAA TCTGAGGACG CCCCTCGTTT CCCAAGTGAA     720

CCTCGTGTGC CAGAAAAACC GCAACATACT CCTCAAAAAA ATCCACAAGA ATCAGATTTT     780

GATAGAGGGT TTTCAGCTGG CTTGAAAGCA AAAAACTCAG GTAGAGGTAT TGATTTTGAA     840

GGTTTCCAGT ATGGTGGCTG GTCAGACGAA TATAAAAAAG GTTACATGCA AGCCTTCGGT     900

ACACCATATA CACCATCAGC AACGTAA                                        927
```

(2) INFORMATION FOR SEQ ID NO:2:

(i) SEQUENCE CHARACTERISTICS:
        (A) LENGTH: 305 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Streptococcus pyogenes
        (B) STRAIN: AP1 (40/58), serotype M1

(xi) SEQUENCE DESCRIPTION: SEQ ID NO:2:

```
Met Asn Ile Arg Asn Lys Ile Glu Asn Ser Lys Thr Leu Leu Phe Thr
1               5                   10                  15

Ser Leu Val Ala Val Ala Leu Leu Gly Ala Thr Gln Pro Val Ser Ala
                20                  25                  30

Glu Thr Tyr Thr Ser Arg Asn Phe Asp Trp Ser Gly Asp Asp Trp Pro
            35                  40                  45

Glu Asp Asp Trp Ser Gly Asp Gly Leu Ser Lys Tyr Asp Arg Ser Gly
        50                  55                  60

Val Gly Leu Ser Gln Tyr Gly Trp Ser Gln Tyr Gly Trp Ser Ser Asp
65                  70                  75                  80

Lys Glu Glu Trp Pro Glu Asp Trp Pro Glu Asp Trp Ser Ser Asp
                85                  90                  95
```

```
Lys Lys Asp Glu Thr Glu Asp Lys Thr Arg Pro Pro Tyr Gly Glu Ala
            100                 105                 110

Leu Gly Thr Gly Tyr Glu Lys Arg Asp Asp Trp Gly Gly Pro Gly Thr
            115                 120                 125

Val Ala Thr Asp Pro Tyr Thr Pro Pro Tyr Gly Gly Ala Leu Gly Thr
    130                 135                 140

Gly Tyr Glu Lys Arg Asp Asp Trp Gly Gly Pro Gly Thr Val Ala Ile
145                 150                 155                 160

Asp Pro Tyr Thr Pro Pro Tyr Gly Glu Ala Leu Gly Thr Gly Tyr Glu
                165                 170                 175

Lys Arg Asp Asp Trp Arg Gly Pro Gly His Ile Pro Lys Pro Glu Asn
            180                 185                 190

Glu Gln Ser Pro Asn Pro Ser His Ile Pro Glu Pro Pro Gln Ile Glu
            195                 200                 205

Trp Pro Gln Trp Asn Gly Phe Asp Glu Leu Ser Phe Gly Pro Ser Asp
        210                 215                 220

Trp Gly Gln Ser Glu Asp Ala Pro Arg Phe Pro Ser Glu Pro Arg Val
225                 230                 235                 240

Pro Glu Lys Pro Gln His Thr Pro Gln Lys Asn Pro Gln Glu Ser Asp
                245                 250                 255

Phe Asp Arg Gly Phe Ser Ala Gly Leu Lys Ala Lys Asn Ser Gly Arg
            260                 265                 270

Gly Ile Asp Phe Glu Gly Phe Gln Tyr Gly Gly Trp Ser Asp Glu Tyr
            275                 280                 285

Lys Lys Gly Tyr Met Gln Ala Phe Gly Thr Pro Tyr Thr Pro Ser Ala
        290                 295                 300

Thr
305

(2) INFORMATION FOR SEQ ID NO:3:

(i) SEQUENCE CHARACTERISTICS:
        (A) LENGTH: 282 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:
        (A) ORGANISM: Streptococcus pyogenes
        (B) STRAIN: Serotype M1
        (C) INDIVIDUAL ISOLATE: U1034

(xi) SEQUENCE DESCRIPTION: SEQ ID NO:3:

Glu Thr Tyr Thr Ser Arg Asn Phe Asp Trp Ser Gly Asp Asp Trp Ser
1               5                   10                  15

Gly Asp Asp Trp Pro Glu Asp Asp Trp Ser Gly Asp Gly Leu Ser Lys
            20                  25                  30

Tyr Asp Arg Ser Gly Val Gly Leu Ser Gln Tyr Gly Trp Ser Lys Tyr
            35                  40                  45

Gly Trp Ser Ser Asp Lys Glu Glu Trp Pro Glu Asp Trp Pro Glu Asp
    50                  55                  60
```

```
Asp Trp Ser Ser Asp Lys Lys Asp Glu Thr Glu Asp Lys Thr Arg Pro
65                  70                  75                  80

Pro Tyr Gly Glu Ala Leu Gly Thr Gly Tyr Glu Lys Arg Asp Asp Trp
            85                  90                  95

Gly Gly Pro Gly Thr Val Ala Thr Asp Pro Tyr Thr Pro Pro Tyr Gly
            100                 105                 110

Gly Ala Leu Gly Thr Gly Tyr Glu Lys Arg Asp Asp Trp Gly Gly Pro
            115                 120                 125

Gly Thr Val Ala Thr Asp Pro Tyr Thr Pro Pro Tyr Gly Gly Ala Leu
            130                 135                 140

Gly Thr Gly Tyr Glu Lys Arg Asp Asp Trp Arg Gly Pro Gly His Ile
145                 150                 155                 160

Pro Lys Pro Glu Asn Asp Gln Ser Pro Asn Pro Ser His Ile Pro Glu
                165                 170                 175

Pro Pro Lys Ile Glu Trp Pro Gln Trp Glu Leu Ala Phe Asp Gly Phe
            180                 185                 190

Asp Glu Leu Ser Phe Gly Pro Ser Asp Trp Gly Gln Ser Glu Asp Ala
            195                 200                 205

Pro Arg Phe Pro Ser Glu Pro Arg Val Pro Glu Lys Pro Gln His Thr
210                 215                 220

Pro Gln Lys Asn Pro Gln Glu Ser Asp Phe Asp Arg Gly Phe Ser Ala
225                 230                 235                 240

Gly Leu Lys Ala Lys Asn Ser Gly Arg Gly Ile Asp Phe Glu Gly Phe
            245                 250                 255

Gln Tyr Gly Gly Trp Ser Asp Glu Tyr Lys Lys Gly Tyr Met Gln Ala
            260                 265                 270

Phe Gly Thr Pro Tyr Thr Pro Ser Ala Thr
            275                 280

(2) INFORMATION FOR SEQ ID NO:4:

(i) SEQUENCE CHARACTERISTICS:
        (A) LENGTH: 134 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:
        (A) ORGANISM: Streptococcus pyogenes
        (B) STRAIN: M1 serotype
        (C) INDIVIDUAL ISOLATE: U1004

(xi) SEQUENCE DESCRIPTION: SEQ ID NO:4:

Glu Thr Tyr Thr Ser Arg Asn Phe Asp Trp Ser Gly Asp Asp Trp Ser
1               5                   10                  15

Gly Asp Asp Trp Pro Glu Asp Asp Trp Ser Gly Asp Gly Leu Ser Lys
            20                  25                  30

Tyr Asp Arg Ser Gly Val Gly Leu Ser Gln Tyr Gly Trp Ser Lys Tyr
            35                  40                  45

Gly Trp Ser Ser Asp Lys Glu Glu Trp Pro Glu Asp Asp Trp Ser Ser
50                  55                  60

Asp Lys Lys Asp Glu Thr Glu Asp Lys Thr Arg Pro Pro Tyr Gly Glu
```

```
                65                  70                  75                  80
            Ala Leu Gly Thr Gly Tyr Glu Lys Arg Asp Asp Trp Gly Pro Gly
                            85                  90                  95

Thr Val Ala Thr Asp Pro Tyr Thr Pro Pro Tyr Gly Gly Ala Leu Gly
                        100                 105                 110

Thr Gly Tyr Glu Lys Arg Asp Asp Trp Gly Gly Pro Gly His Ile Pro
                    115                 120                 125

Lys Pro Glu Asn Glu Gln
                130
```

(2) INFORMATION FOR SEQ ID NO:5:

(i) SEQUENCE CHARACTERISTICS:
        (A) LENGTH: 849 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes
        (B) STRAIN: M1 serotype
        (C) INDIVIDUAL ISOLATE: U1034

(xi) SEQUENCE DESCRIPTION: SEQ ID NO:5:

```
GAAACGTATA CATCACGCAA TTTTGACTGG TCTGGAGATG ACTGGTCTGG AGATGACTGG      60

CCTGAAGATG ACTGGTCTGG AGATGGTTTG TCTAAATATG ACCGGTCTGG AGTTGGTTTG     120

TCTCAATATG GCTGGTCTAA ATATGGCTGG TCTAGCGATA AGAAGAATG GCCTGAAGAT      180

TGGCCTGAAG ATGACTGGTC TAGCGATAAA AAGATGAGA CAGAAGATAA AACGAGACCA      240

CCATATGGAG AAGCATTAGG TACAGGGTAT GAAAAACGTG ATGATTGGGG AGGACCTGGT     300

ACGGTGGCAA CTGACCCTTA CACTCCACCA TATGGAGGAG CATTAGGTAC AGGGTATGAA     360

AAACGTGATG ATTGGGGAGG ACCTGGTACG GTGGCAACTG ACCCTTACAC CCCACCATAT     420

GGAGGAGCAT TAGGTACAGG GTATGAAAAA CGTGATGATT GGAGAGGACC TGGACATATC     480

CCTAAACCTG AGAACGACCA ATCACCAAAC CCATCTCATA TTCCTGAACC TCCTAAGATT     540

GAGTGGCCTC AGTGGGAATT GGCCTTTGAT GGCTTTGATG AATTATCATT TGGCCCCTCT     600

GATTGGGGCC AATCTGAGGA CGCCCCTCGT TTCCCAAGTG AACCTCGTGT GCCAGAAAAA     660

CCGCAACATA CTCCTCAAAA AAATCCACAA GAATCAGATT TTGATAGAGG GTTTTCAGCT     720

GGCTTGAAAG CAAAAAACTC AGGTAGAGGT ATTGATTTTG AAGGTTTCCA GTATGGTGGC     780

TGGTCAGACG AATATAAAAA AGGTTACATG CAAGCCTTCG GTACACCATA TACACCATCA     840

GCAACGTAA                                                             849
```

(2) INFORMATION FOR SEQ ID NO:6:

(i) SEQUENCE CHARACTERISTICS:
        (A) LENGTH: 402 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Streptococcus pyogenes
            (B) STRAIN: M1 serotype
            (C) INDIVIDUAL ISOLATE: U1004

(xi) SEQUENCE DESCRIPTION: SEQ ID NO:6:

```
GAAACGTATA CATCACGCAA TTTTGACTGG TCTGGAGATG ACTGGTCTGG AGATGACTGG      60

CCTGAAGATG ACTGGTCTGG AGATGGTTTG TCTAAATATG ACCGGTCTGG AGTTGGTTTG     120

TCTCAATATG GCTGGTCTAA ATATGGCTGG TCTAGCGATA AGAAGAATG GCCTGAAGAT      180

GACTGGTCTA GCGATAAAAA AGATGAGACA GAAGATAAAA CGAGACCACC ATATGGAGAA     240

GCATTAGGTA CAGGGTATGA AAAACGTGAT GATTGGGGAG GACCTGGTAC GGTGGCAACT     300

GACCCTTACA CTCCACCATA TGGAGGAGCA TTAGGTACAG GGTATGAAAA ACGTGATGAT     360

TGGGGAGGAC CCGGACATAT TCCCAAACCT GAGAACGAAC AA                       402
```

(2) INFORMATION FOR SEQ ID NO:7:

(i) SEQUENCE CHARACTERISTICS:
            (A) LENGTH: 8 amino acids
            (B) TYPE: amino acid
            (C) STRANDEDNESS:
            (D) TOPOLOGY: linear (xi) SEQUENCE DESCRIPTION: SEQ ID NO:7:

```
Glu Thr Tyr Thr Ser Arg Asn Phe
 1               5
```

(2) INFORMATION FOR SEQ ID NO:8:

(i) SEQUENCE CHARACTERISTICS:
            (A) LENGTH: 12 amino acids
            (B) TYPE: amino acid
            (C) STRANDEDNESS:
            (D) TOPOLOGY: linear (xi) SEQUENCE DESCRIPTION: SEQ ID NO:8:

```
Asp Trp Ser Gly Asp Asp Trp Pro Glu Asp Asp Trp
 1               5                  10
```

(2) INFORMATION FOR SEQ ID NO:9:

(i) SEQUENCE CHARACTERISTICS:
            (A) LENGTH: 12 amino acids
            (B) TYPE: amino acid
            (C) STRANDEDNESS:
            (D) TOPOLOGY: linear (xi) SEQUENCE DESCRIPTION: SEQ ID NO:9:

```
Arg Ser Gly Val Gly Leu Ser Gln Tyr Gly Trp Ser
 1               5                  10
```

(2) INFORMATION FOR SEQ ID NO:10:

(i) SEQUENCE CHARACTERISTICS:
            (A) LENGTH: 13 amino acids
            (B) TYPE: amino acid
            (C) STRANDEDNESS:
            (D) TOPOLOGY: linear (xi) SEQUENCE DESCRIPTION: SEQ ID NO:10:

```
Trp Ser Ser Asp Lys Lys Asp Glu Thr Glu Asp Lys Thr
 1               5                  10
```

(2) INFORMATION FOR SEQ ID NO:11:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:11:

```
Gly Thr Gly Tyr Glu Lys Arg Asp Asp Trp Gly Gly Pro Gly
1               5                   10
```

(2) INFORMATION FOR SEQ ID NO:12:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:12:

```
Lys Arg Asp Asp Trp Arg Gly Pro Gly His Ile Pro Lys Pro
1               5                   10
```

(2) INFORMATION FOR SEQ ID NO:13:

(i) SEQUENCE CHARACTERISTICS:
        (A) LENGTH: 1204 base pairs
        (B) TYPE: nucleic acid
        (C) STRANDEDNESS: single
        (D) TOPOLOGY: linear (xi) SEQUENCE DESCRIPTION: SEQ ID NO:13:

```
GCTATCACTT TCTAATACTG AGTGAACATC AAGAGAGAAC CAGTCGGTTC TCTCTTTTAT      60
GTATAGAAGA ATGAGGTTAA GGAGAGGTCA CAAACTAAAC AACTCTTAAA AAGCTGACCT     120
TTACTAATAA TCGTCTTTGT TTTATAATGA AAACATTAAC GAAATAATTT ATTAAGGAGA     180
GAATACTAAT GAATATTAGA AATAAGATTG AAAATAGTAA AACACTACTA TTTACATCCC     240
TTGTAGCCGT GGCTCTACTA GGAGCTACAC AACCAGTTTC AGCCGAAACG TATACATCAC     300
GCAATTTTGA CTGGTCTGGA GATGACTGGC CTGAAGATGA CTGGTCTGGA GATGGTTTGT     360
CTAAATATGA CCGGTCTGGA GTTGGTTTGT CTCAATATGG CTGGTCTCAA TATGGCTGGT     420
CTAGCGATAA AGAAGAATGG CCTGAAGATT GGCCTGAAGA TGACTGGTCT AGCGATAAAA     480
AAGATGAGAC AGAAGATAAA ACGAGACCAC CATATGGAGA AGCATTAGGT ACAGGGTATG     540
AAAAACGTGA TGATTGGGGA GGACCTGGTA CGGTGGCAAC TGACCCTTAC ACTCCACCAT     600
ATGGAGGAGC ATTAGGTACA GGGTATGAAA ACGTGATGA TTGGGGAGGA CCTGGTACGG     660
TAGCAATTGA CCCTTACACT CCACCATATG GAGAAGCATT AGGTACAGGG TATGAAAAAC     720
GTGATGATTG GAGAGGACCT GGACATATTC CTAAACCTGA GAACGAACAA TCACCAAACC     780
CATCTCATAT TCCTGAACCT CCTCAGATTG AGTGGCCTCA GTGGAATGGC TTTGATGAAT     840
TATCATTTGG CCCCTCTGAT TGGGGCCAAT CTGAGGACGC CCCTCGTTTC CAAGTGAAC     900
CTCGTGTGCC AGAAAAACCG CAACATACTC CTCAAAAAAA TCCACAAGAA TCAGATTTTG     960
ATAGAGGGTT TTCAGCTGGC TTGAAAGCAA AAAACTCAGG TAGAGGTATT GATTTTGAAG    1020
GTTTCCAGTA TGGTGGCTGG TCAGACGAAT ATAAAAAAGG TTACATGCAA GCCTTCGGTA    1080
CACCATATAC ACCATCAGCA ACGTAAAGGG ATGCGATAGG AATAGTTTAG TGCTGCTTTT    1140
GCCACGCTTC TTAGGGATTT TTACGAAAAA TTCTGATTCC ATAGGTGATG TAGGGCTGTA    1200
```

AAAT                                                              1204

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:14:

Glu Thr Tyr Thr Ser
1               5

(2) INFORMATION FOR SEQ ID NO:15:

(i) SEQUENCE CHARACTERISTICS:
        (A) LENGTH: 10 amino acids
        (B) TYPE: amino acid
        (C) STRANDEDNESS:
        (D) TOPOLOGY: linear (xi) SEQUENCE DESCRIPTION: SEQ ID NO:15:

Asp Gln Thr Val Ser Asp Asn Glu Leu Gln
1               5                   10

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS:
        (D) TOPOLOGY: linear (xi) SEQUENCE DESCRIPTION: SEQ ID NO:16:

Ser Leu Met Pro Phe Ser Pro Tyr Glu Pro
1               5                   10

(2) INFORMATION FOR SEQ ID NO:17:

(i) SEQUENCE CHARACTERISTICS:
        (A) LENGTH: 10 amino acids
        (B) TYPE: amino acid
        (C) STRANDEDNESS:
        (D) TOPOLOGY: linear (xi) SEQUENCE DESCRIPTION: SEQ ID NO:17:

Val Ser Pro Thr Asp Cys Ser Ala Val Glu
1               5                   10

(2) INFORMATION FOR SEQ ID NO:18:

(i) SEQUENCE CHARACTERISTICS:
        (A) LENGTH: 273 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:
        (A) ORGANISM: Streptococcus pyogenes
        (B) STRAIN: Serotype M1

(xi) SEQUENCE DESCRIPTION: SEQ ID NO:18:

Glu Thr Tyr Thr Ser Arg Asn Phe Asp Trp Ser Gly Asp Asp Trp Pro
1               5                   10                  15

Glu Asp Asp Trp Ser Gly Asp Gly Leu Ser Lys Tyr Asp Arg Ser Gly
                20                  25                  30

Val Gly Leu Ser Gln Tyr Gly Trp Ser Gln Tyr Gly Trp Ser Ser Asp
            35                  40                  45

Lys Glu Glu Trp Pro Glu Asp Trp Pro Glu Asp Asp Trp Ser Ser Asp
50                      55                  60

Lys Lys Asp Glu Thr Glu Asp Lys Thr Arg Pro Pro Tyr Gly Glu Ala
65                  70                  75                  80

Leu Gly Thr Gly Tyr Glu Lys Arg Asp Asp Trp Gly Gly Pro Gly Thr
                85                  90                  95

Val Ala Thr Asp Pro Tyr Thr Pro Pro Tyr Gly Gly Ala Leu Gly Thr
            100                 105                 110

Gly Tyr Glu Lys Arg Asp Asp Trp Gly Gly Pro Gly Thr Val Ala Ile
            115                 120                 125

Asp Pro Tyr Thr Pro Pro Tyr Gly Glu Ala Leu Gly Thr Gly Tyr Glu
        130                 135                 140

Lys Arg Asp Asp Trp Arg Gly Pro Gly His Ile Pro Lys Pro Glu Asn
145                 150                 155                 160

Glu Gln Ser Pro Asn Pro Ser His Ile Pro Glu Pro Pro Gln Ile Glu
                165                 170                 175

Trp Pro Gln Trp Asn Gly Phe Asp Glu Leu Ser Phe Gly Pro Ser Asp
                180                 185                 190

Trp Gly Gln Ser Glu Asp Ala Pro Arg Phe Pro Ser Glu Pro Arg Val
            195                 200                 205

Pro Glu Lys Pro Gln His Thr Pro Gln Lys Asn Pro Gln Glu Ser Asp
210                 215                 220

Phe Asp Arg Gly Phe Ser Ala Gly Leu Lys Ala Lys Asn Ser Gly Arg
225                 230                 235                 240

Gly Ile Asp Phe Glu Gly Phe Gln Tyr Gly Trp Ser Asp Glu Tyr
                245                 250                 255

Lys Lys Gly Tyr Met Gln Ala Phe Gly Thr Pro Tyr Thr Pro Ser Ala
                260                 265                 270

Thr (2) INFORMATION FOR SEQ ID NO:19:

(i) SEQUENCE CHARACTERISTICS:
        (A) LENGTH: 133 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:
        (A) ORGANISM: Streptococcus pyogenes
        (B) STRAIN: Serotype M1

(xi) SEQUENCE DESCRIPTION: SEQ ID NO:19:

Glu Thr Tyr Thr Ser Arg Asn Phe Asp Trp Ser Asp Asp Trp Ser Gly

-continued

```
1               5                    10                   15
Asp Asp Trp Pro Glu Asp Asp Trp Ser Gly Asp Gly Leu Ser Lys Tyr
            20                  25                  30
Asp Arg Ser Gly Val Gly Leu Ser Gln Tyr Gly Trp Ser Lys Tyr Gly
            35                  40                  45
Trp Ser Ser Asp Lys Glu Glu Trp Pro Glu Asp Asp Trp Ser Ser Asp
    50                  55                  60
Lys Lys Asp Glu Thr Glu Asp Lys Thr Arg Pro Pro Tyr Gly Glu Ala
65                  70                  75                  80
Leu Gly Thr Gly Tyr Glu Lys Arg Asp Asp Trp Gly Gly Pro Gly Thr
                85                  90                  95
Val Ala Thr Asp Pro Tyr Thr Pro Pro Tyr Gly Gly Ala Leu Gly Thr
            100                 105                 110
Gly Tyr Glu Lys Arg Asp Asp Trp Gly Gly Pro Gly His Ile Pro Lys
        115                 120                 125
Pro Glu Asn Glu Gln
        130
```